US007915042B2

(12) United States Patent
Comer et al.

(10) Patent No.: US 7,915,042 B2
(45) Date of Patent: Mar. 29, 2011

(54) KERATINOCYTES EXPRESSING EXOGENOUS ANGIOGENIC GROWTH FACTORS

(75) Inventors: Allen R. Comer, Madison, WI (US);
Michael Hoffmann, Madison, WI (US);
B. Lynn Allen-Hoffmann, Madison, WI (US)

(73) Assignee: Stratatech Corporation, Madison, WI (US)

( * ) Notice: Subject to any disclaimer, the term of this patent is extended or adjusted under 35 U.S.C. 154(b) by 52 days.

(21) Appl. No.: 12/392,221

(22) Filed: Feb. 25, 2009

(65) Prior Publication Data
US 2009/0169528 A1 Jul. 2, 2009

Related U.S. Application Data

(63) Continuation of application No. 10/425,784, filed on Apr. 29, 2003, now Pat. No. 7,498,167.

(60) Provisional application No. 60/376,488, filed on Apr. 30, 2002.

(51) Int. Cl.
*C12N 5/08* (2006.01)
*A01N 43/04* (2006.01)
*C12N 5/00* (2006.01)
*A01N 63/00* (2006.01)
*C07H 21/02* (2006.01)

(52) U.S. Cl. ............... 435/371; 424/93.21; 424/422; 424/423; 435/240; 435/395; 435/455; 514/44; 536/23.1; 536/23.5

(58) Field of Classification Search .............. 424/93.21, 424/423, 422; 435/240, 371, 395, 455, 6, 435/91.1; 536/23.1, 23.5; 514/44
See application file for complete search history.

(56) References Cited

U.S. PATENT DOCUMENTS

| | | | |
|---|---|---|---|
| 4,485,096 A | 11/1984 | Rell | |
| 5,292,655 A | 3/1994 | Wille, Jr. | |
| 5,536,656 A | 7/1996 | Kemp et al. | |
| 5,658,331 A | 8/1997 | Della Valle | |
| 5,693,332 A * | 12/1997 | Hansbrough | 424/426 |
| 5,968,546 A | 10/1999 | Bauer et al. | |
| 5,989,837 A | 11/1999 | Allen-Hoffmann et al. | |
| 6,039,760 A * | 3/2000 | Eisenberg | 623/15.12 |
| 6,458,382 B1 | 10/2002 | Herweijer | |
| 6,838,430 B2 | 1/2005 | Arbeit | |
| 6,846,675 B2 | 1/2005 | Conrad | |
| 6,849,718 B2 | 2/2005 | Kaelin, Jr. | |
| 2002/0187498 A1 | 12/2002 | Comer et al. | |
| 2004/0146881 A1 | 7/2004 | Allen-Hoffmann et al. | |
| 2004/0190793 A1 | 9/2004 | Rorvig et al. | |
| 2005/0013807 A1 | 1/2005 | Comer et al. | |
| 2005/0079578 A1 | 4/2005 | Centanni et al. | |
| 2005/0186185 A1 | 8/2005 | Conrad et al. | |

OTHER PUBLICATIONS

Baumgartner, Therapeutic Angiogenesis:Theoretic Problems UsingVascular Endothelial Growth Factor Curr Cardiol Rep 2:24-8. (2000).
Bellomo, et al., Mice Lacking the Vascular Endothelial Growth Factor-B Gene (Vegfb) Have Smaller Hearts, Dysfunctional Coronary Vasculature, and Impaired Recovery From Cardiac Ischemia Circ Res 86:E29-35. (2000).
Carmeliet, et al., Abnormal BloodVessel Development and Lethality in Embryos Lacking a SingleVEGF Allele Nature 380:435-9. (1996).
Carmeliet, Mechanisms of Angiogenesis and Arteriogenesis, Nat Med 6:389-95. (2000).
Del Rio, et al.,Nonviral Transfer of Genes to Pig Primary Keratinocytes. Induction of Angiogenesis by Composite Grafts of Modified Keratinocytes Overexpressing VEGF Driven by a Keratin Promoter Gene Therapy 6:1734-1741 (1999).
Eriksson and Alitalo, Structure, Expression and Receptor-Binding Properties of Novel Vascular Endothelial Growth Factors, Curr Top Microbiol Immunol 237:41-57 (1999).
Ferrara and Henzel, Pituitary Follicular Cells Secrete a Novel Heparin-Binding Growth Factor Specific for Vascular Endothilial Cells Biochem Biophys Res Commun 161:851-8 (1989).
Ferrara, et al., Purification and Cloning of Vascular Endothelial Growth Factor Secreted by Pituitary Folliculostellate Cells Methods Enzymol 198:391-405. (1991).
Ferrara, et al., Heterozygous Embryonic Lethality Induced by Targeted Inactivation of the VEGF Gene Nature 380:439-42. (1996).
Gamble, et al.,Angiopoietin-I Is an Antipermeability and Anti-Inflammatory Agent In Vitro and Targets Cell Junctions Circ Res 87:603-7. (2000).
Gerdes, et al., Cell Cycle Analysis of a Cell Proliferation-Associated Human Nuclear Antigen Defined by the Monoclonal Antibody Ki-671 J Immunol 133:1710-5. (1984).
Houck, et al., The Vascular Endothelial Growth Factor Family: Identification of a Fourth Molecular Species and Characterization of Alternative Splicing of RNA Mol Endocrinol 5:1806-14. (1991).
Huang, et al., Activation of Hypoxia-inducible Transcription Factor Depends Primarily upon Redox-sensitive Stabilization of Its a Subunit J. Biol. Chem., 271, 32253-32259 (1996).
Larcher, et al., VEGFjVPF Overexpression in Skin of Transgenic Mice Induces Angiogenesis, Vascular Hyperpermeability and Accelerated Tumor Development Oncogene 17:303-11. (1998).
Lopez, et al., The Labeling of Proliferating Cells by Ki67 and MIB-1 Antibodies Depends on the Binding of a Nuclear Protein to the DNA Exp Cell Res 210:145-53. (1994).
Maisonpierre, et al., Angiopoietin-2. a Natural Antagonist for Tie2 That Disrupts in vivo Angiogenesis Science 277:55-60. (1997).

(Continued)

*Primary Examiner* — Jane Zara
(74) *Attorney, Agent, or Firm* — Casimir Jones SC

(57) ABSTRACT

The present invention relates to in vitro cultured skin tissue, and in particular to cultured skin tissue comprising exogenous genes encoding angiogenic growth factors. In some embodiments, the keratinocytes express exogenous angiopoietin-1 or a member of the VEGF family, preferably VEGF-A. In particularly preferred embodiments, the keratinocytes are incorporated into cultured skin tissue.

3 Claims, 5 Drawing Sheets

OTHER PUBLICATIONS

O'Brien and Simari, Gene Therapy for Atherosclerotic Cardiovascular Disease: A Time for Optimism and Caution Mayo Clin Proc 75:831-4. (2000).

Olofsson, et al., Current biology of VEGF-B and VEGF-C Curr Opin Biotechnol 10:528-35. (1999).

Papapetropoulos, et al., Direct Actions of Angiopoietin-1 on Human Endothelium: Evidence for Network Stabilization, Cell Survival, and Interaction with Other Angiogenic Growth FactorsLab Invest 79:213-23. (1999).

Persico, et al., Structure, Expression and Receptor-Binding Properties of Placenta Growth Factor (PIGF) Curr Top Microbiol Immunol 237:31-40. (1999).

Rio, et al., Gene Therapy, 6:1734-1741 (1999).

Sato, et al., Distinct Roles of the Receptor Tyrosine Kinases Tie-I and Tie-2 in Blood Vessel Formation Nature 376:70-4. (1995).

Schroeder and Neagle, FLIPR: A New Instrument for Accurate, High Throughput Optical Screening J. Biomol. Screening 1:75-80 [1996].

Senger, et al., Tumor Cells Secrete a Vascular Permeability Factor That Promotes Accumulation of Ascites Fluid Science 219:983-5. (1983).

Thurston, et al., Leakage-Resistant Blood Vessels in Mice Transgenically Overexpressing Angiopoietin-1 Science 286:2511-4. (1999).

Vale, et al.,Left Ventricular Electromechanical Mapping to Assess Efficacy of phVEGF165 Gene Transfer for Therapeutic Angiogenesis in Chronic Myocardial Ischemia Circulation 102:965-74 (2000).

Wang, et al., Positive and Negative Regulation of Gene Expression in Eukaryotic Cells With an Inducible Transcriptional Regulator Gene Ther 4:432-41. (1997).

Wang, et al., A Regulatory System For Use in Gene Transfer Proc Natl Acad Sci U S A 91:8180-4. (1994).

ISR PCT/US03/13327.

Supp, et al., "Enhanced Vascularization of Cultured Skin Substitutes Genetically Modified to Overexpress Vascular Endothelial Growth Factor," The Journal of Investigative Dermatology 114, 5-13. (2000).

Boyce et al., J. Burn Care Rehab. 20(6):453-461 (1999).
Auger et al., In Vitro Cell. Dev. Biol.—Animal 36:96-103.
Asbill et al., Pharm. Research 17(9): 1092-97 (2000).
Meana et al., Burns 24:621-30 (1998).
Baden, In Vitro Cell. Dev. Biol. 23(3):205-213 (1987).
Boucamp et al., J. cell. Boil. 106:761-771 (1988).
Allen-Hoffmann et al., J. Invest. Dermatol., 114(3): 444-455 (2000).
Yancopoulos, et al., Nature 407:242-8. (2000).
Shalaby, et al., Nature 376:62-6. (1995).
Fong, et al., Nature 376:66-70. (1995).
Carmeliet, et al., Nature 380:435-9. (1996).
Ferrara, et al., Nature 380:439-42. (1996).
Maisonpierre, et al., Science 277:55-60. (1997).
Moller, et al., Mol Hum Reprod 7:65-72. (2001).
Brown, et al., J Exp Med 176:1375-9. (1992).
Detmar, et al., J Exp Med 180:1141-6. (1994).
Shweiki, et al., Proc Natl Acad Sci U S A 92:768-72. (1995).
Ballaun, et al., J Invest Dermatol 104:7-10. (1995).
Detmar, et al., J Invest Dermatol 108:263-8. (1997).
Frank, et al., J Biol Chem 270:12607-13. (1995).
Rivard, et al., Am J Pathol 154:355-63. (1999).
Davis, et al., Cell 87:1161-9. (1996).
Suri, et al., Cell 87:1171-80. (1996).
Gamble, et al., Circ Res 87:603-7. (2000).
Detmar, et al., J Invest Dermatol 111:1-6. (1998).
Thurston, et al., Science 286:2511-4. (1999).
Suri, et al., Science 282:468-71. (1998).
Taub, et al., Plast Reconstr Surg 102:2033-9. (1998).
Tanaka, et al., J Thorac Cardiovasc Surg 120:720-8. (2000).
Del Rio, et al., Gene Therapy 6:1734-1741 (1999).
Myers et al., A. J. Surg. 170(1):75-83 (1995).
Detmar, et al., J Invest Dermatol 105:44-50. (1995).
Nehls and Drenckhahn, Microvasc Res 50:311-22. (1995).
Koblizek, et al., Curr Biol 8:529-32. (1998).
Bruick, et al., "Building Better Vasculatrue," Genes Dev. 2001. 15(19):2497-2502.

* cited by examiner

Figure 1

Nucleic acid sequence for VEGF (coding region in capital letters)

ccATGAACTTTCTGCTGTCTTGGGTGCATTGGAGCCTTGCCTTGCTGCTCTACCTCCACCATGCCAAGTGG
TCCCAGGCTGCACCCATGGCAGAAGGAGGAGGGCAGAATCATCACGAAGTGGTGAAGTTCATGGATGTCTA
TCAGCGCAGCTACTGCCATCCAATCGAGACCCTGGTGGACATCTTCCAGGAGTACCCTGATGAGATCGAGT
ACATCTTCAAGCCATCCTGTGTGCCCCTGATGCGATGCGGGGGCTGCTGCAATGACGAGGGCCTGGAGTGT
GTGCCCACTGAGGAGTCCAACATCACCATGCAGATTATGCGGATCAAACCTCACCAAGGCCAGCACATAGG
AGAGATGAGCTTCCTACAGCACAACAAATGTGAATGCAGACCAAAGAAAGATAGAGCAAGACAAGAAAATC
CCTGTGGGCCTTGCTCAGAGCGGAGAAAGCATTTGTTTGTACAAGATCCGCAGACGTGTAAATGTTCCTGC
AAAAACACAGACTCGCGTTGCAAGGCGAGGCAGCTTGAGTTAAACGAACGTACTTGCAGATGTGACAAGCC
GAGGCGGTGAgccgggcaggaggaaggagcctccctcagggtttcgggaaccagatctctcaccaggaaag
actgatacagaacgatcga

Figure 2

Nucleic acid sequence for Ang-1 (coding region in capital letters)

cagctgactcaggcaggctccatgctgaacggtcacacagagaggaaacaataaatctca
gctactatgcaataaatatctcaagttttaacgaagaaaaacatcattgcagtgaaataa
aaaattttaaaattttagaacaaagctaacaaatggctagttttctatgattcttcttca
aacgctttctttgagggggaaagagtcaaacaaacaagcagtttttacctgaaataaagaa
ctagttttagaggtcagaagaaaggagcaagttttgcgagaggcacggaaggagtgtgct
ggcagtacaATGACAGTTTTCCTTTCCTTTGCTTTCCTCGCTGCCATTCTGACTCACATA
GGGTGCAGCAATCAGCGCCGAAGTCCAGAAAACAGTGGGAGAAGATATAACCGGATTCAA
CATGGGCAATGTGCCTACACTTTCATTCTTCCAGAACACGATGGCAACTGTCGTGAGAGT
ACGACAGACCAGTACAACACAAACGCTCTGCAGAGAGATGCTCCACACGTGGAACCGGAT
TTCTCTTCCCAGAAACTTCAACATCTGGAACATGTGATGGAAAATTATACTCAGTGGCTG
CAAAAACTTGAGAATTACATTGTGGAAAACATGAAGTCGGAGATGGCCCAGATACAGCAG
AATGCAGTTCAGAACCACACGGCTACCATGCTGGAGATAGGAACCAGCCTCCTCTCTCAG
ACTGCAGAGCAGACCAGAAAGCTGACAGATGTTGAGACCCAGGTACTAAATCAAACTTCT
CGACTTGAGATACAGCTGCTGGAGAATTCATTATCCACCTACAAGCTAGAGAAGCAACTT
CTTCAACAGACAAATGAAATCTTGAAGATCCATGAAAAAACAGTTTATTAGAACATAAA
ATCTTAGAAATGGAAGGAAAACACAAGGAAGAGTTGGACACCTTAAAGGAAGAGAAAGAG
AACCTTCAAGGCTTGGTTACTCGTCAAACATATATAATCCAGGAGCTGGAAAAGCAATTA
AACAGAGCTACCACCAACAACAGTGTCCTTCAGAAGCAGCAACTGGAGCTGATGGACACA
GTCCACAACCTTGTCAATCTTTGCACTAAAGAAGGTGTTTTACTAAAGGGAGGAAAAGA
GAGGAAGAGAAACCATTTAGAGACTGTGCAGATGTATATCAAGCTGGTTTTAATAAAAGT
GGAATCTACACTATTTATATTAATAATATGCCAGAACCCAAAAAGGTGTTTTGCAATATG
GATGTCAATGGGGGAGGTTGGACTGTAATACAACATCGTGAAGATGGAAGTCTAGATTTC
CAAAGAGGCTGGAAGGAATATAAAATGGGTTTTGGAAATCCCTCCGGTGAATATTGGCTG
GGGAATGAGTTTATTTTTGCCATTACCAGTCAGAGGCAGTACATGCTAAGAATTGAGTTA
ATGGACTGGGAAGGGAACCGAGCCTATTCACAGTATGACAGATTCCACATAGGAAATGAA
AAGCAAAACTATAGGTTGTATTTAAAAGGTCACACTGGGACAGCAGGAAAACAGAGCAGC
CTGATCTTACACGGTGCTGATTTCAGCACTAAAGATGCTGATAATGACAACTGTATGTGC
AAATGTGCCCTCATGTTAACAGGAGGATGGTGGTTTGATGCTTGTGGCCCCTCCAATCTA
AATGGAATGTTCTATACTGCGGGACAAAACCATGGAAAACTGAATGGGATAAAGTGGCAC
TACTTCAAAGGGCCCAGTTACTCCTTACGTTCCACAACTATGATGATTCGACCTTTAGAT
TTTTGAaagcgcaatgtcagaagcgattatgaaagcaacaaagaaatccggagaagctgc
caggtgagaaactgtttgaaaacttcagaagcaaacaatattgtctcccttccagcaata
agtggtagttatgtgaagtcaccaaggttcttgaccgtgaatctggagccgtttgagttc
acaagagtctctacttggggtgacagtgctcacgtggctcgactatagaaaactccactg
actgtcgggcttaaaaagggaagaaactgctgagcttgctgtgcttcaaactactactg
gaccttatttggaactatggtagccagatgataaatatggttaatttc

Figure 3a

Nucleic acid sequence for HIF-1 (Coding region in capital letters)

```
cacgaggcagcactctcttcgtcgcttcggccagtgtgtcgggctgggccctgacaagcc
acctgaggagaggctcggagccgggcccggaccccggcgattgccgcccgcttctctcta
gtctcacgaggggtttcccgcctcgcaccccacctctggacttgcctttccttctcttc
tccgcgtgtggagggagccagcgcttaggccggagcgagcctgggggccgccgccgtga
agacatcgcggggaccgattcaccATGGAGGGCGCCGGCGGCGCGAACGACAAGAAAAAG
ATAAGTTCTGAACGTCGAAAAGAAAAGTCTCGAGATGCAGCCAGATCTCGGCGAAGTAAA
GAATCTGAAGTTTTTTATGAGCTTGCTCATCAGTTGCCACTTCCACATAATGTGAGTTCG
CATCTTGATAAGCCTCTGTGATGAGGCTTACCATCAGCTATTTGCGTGTGAGGAAACTT
CTGGATGCTGGTGATTTGGATATTGAAGATGACATGAAAGCACAGATGAATTGCTTTTAT
TTGAAAGCCTTGGATGGTTTTGTTATGGTTCTCACAGATGATGGTGACATGATTTACATT
TCTGATAATGTGAACAAATACATGGGATTAACTCAGTTTGAACTAACTGGACACAGTGTG
TTTGATTTTACTCATCCATGTGACCATGAGGAAATGAGAGAAATGCTTACACACAGAAAT
GGCCTTGTGAAAAAGGGTAAAGAACAAAACACACAGCGAAGCTTTTTTCTCAGAATGAAG
TGTACCCTAACTAGCCGAGGAAGAACTATGAACATAAAGTCTGCAACATGGAAGGTATTG
CACTGCACAGGCCACATTCACGTATATGATACCAACAGTAACCAACCTCAGTGTGGGTAT
AAGAAACCACCTATGACCTGCTTGGTGCTGATTTGTGAACCCATTCCTCACCCATCAAAT
ATTGAAATTCCTTTAGATAGCAAGACTTTCCTCAGTCGACACAGCCTGGATATGAAATTT
TCTTATTGTGATGAAAGAATTACCGAATTGATGGGATATGAGCCAGAAGAACTTTTAGGC
CGCTCAATTTATGAATATTATCATGCTTTGGACTCTGATCATCTGACCAAAACTCATCAT
GATATGTTTACTAAAGGACAAGTCACCACAGGACAGTACAGGATGCTTGCCAAAAGAGGT
GGATATGTCTGGGTTGAAACTCAAGCAACTGTCATATATAACACCAAGAATTCTCAACCA
CAGTGCATTGTATGTGTGAATTACGTTGTGAGTGGTATTATTCAGCACGACTTGATTTTC
TCCCTTCAACAAACAGAATGTGTCCTTAAACCGGTTGAATCTTCAGATATGAAAATGACT
CAGCTATTCACCAAAGTTGAATCAGAAGATACAAGTAGCCTCTTTGACAAACTTAAGAAG
GAACCTGATGCTTTAACTTTGCTGGCCCCAGCCGCTGGAGACACAATCATATCTTTAGAT
TTTGGCAGCAACGACACAGAAACTGATGACCAGCAACTTGAGGAAGTACCATTATATAAT
GATGTAATGCTCCCCTCACCCAACGAAAAATTACAGAATATAAATTTGGCAATGTCTCCA
TTACCCACCGCTGAAACGCCAAAGCCACTTCGAAGTAGTGCTGACCCTGCACTCAATCAA
GAAGTTGCATTAAAATTAGAACCAAATCCAGAGTCACTGGAACTTTCTTTTACCATGCCC
CAGATTCAGGATCAGACACCTAGTCCTTCCGATGGAAGCACTAGACAAAGTTCACCTGAG
CCTAATAGTCCCAGTGAATATTGTTTTTATGTGGATAGTGATATGGTCAATGAATTCAAG
TTGGAATTGGTAGAAAAACTTTTTGCTGAAGACACAGAAGCAAAGAACCCATTTTCTACT
CAGGACACAGATTTAGACTTGGAGATGTTAGCTCCCTATATCCCAATGGATGATGACTTC
CAGTTACGTTCCTTCGATCAGTTGTCACCATTAGAAAGCAGTTCCGCAAGCCCTGAAAGC
GCAAGTCCTCAAAGCACAGTTACAGTATTCCAGCAGACTCAAATACAAGAACCTACTGCT
AATGCCACCACTACCACTGCCACCACTGATGAATTAAAAACAGTGACAAAAGACCGTATG
GAAGACATTAAAATATTGATTGCATCTCCATCTCCTACCCACATACATAAAGAAACTACT
AGTGCCACATCATCACCATATAGAGATACTCAAAGTCGGACAGCCTCACCAAACAGAGCA
GGAAAAGGAGTCATAGAACAGACAGAAAAATCTCATCCAAGAAGCCCTAACGTGTTATCT
GTCGCTTTGAGTCAAAGAACTACAGTTCCTGAGGAAGAACTAAATCCAAAGATACTAGCT
TTGCAGAATGCTCAGAGAAAGCGAAAAATGGAACATGATGGTTCACTTTTTCAAGCAGTA
GGAATTGGAACATTATTACAGCAGCCAGACGATCATGCAGCTACTACATCACTTTCTTGG
AAACGTGTAAAAGGATGCAAATCTAGTGAACAGAATGGAATGGAGCAAAAGACAATTATT
TTAATACCCTCTGATTTAGCATGTAGACTGCTGGGGCAATCAATGGATGAAAGTGGATTA
CCACAGCTGACCAGTTATGATTGTGAAGTTAATGCTCCTATACAAGGCAGCAGAAACCTA
CTGCAGGGTGAAGAATTACTCAGAGCTTTGGATCAAGTTAACTGAgcttttcttaattt
cattcctttttttggacactggtggctcactacctaaagcagtctatttatattttctac
atctaattttagaagcctggctacaatactgcacaaacttggttagttcaattttgatc
cccttctacttaatttacattaatgctcttttttagtatgttctttaatgctggatcac
agacagctcatttctcagttttttggtatttaaaccattgcattgcagtagcatcattt
taaaaaatgcaccttttattatttattttggctagggagtttatcccttttcgaat
tattttaagaagatgccaatataattttgtaagaaggcagtaacctttcatcatgatc
ataggcagttgaaaaattttacaccttttttttcacattttacataaataataatgctt
```

Figure 3b

```
tgccagcagtacgtggtagccacaattgcacaatatattttcttaaaaaataccagcagt
tactcatggaatatattctgcgtttataaaactagttttttaagaagaaattttttttggc
ctatgaaattgttaaacctggaacatgacattgttaatcatataataatgattcttaaat
gctgtatggtttattatttaaatgggtaaagccatttacataatatagaaagatatgcat
atatctagaaggtatgtggcatttatttggataaaattctcaattcagagaaatcatctg
atgtttctatagtcactttgccagctcaaaagaaaacaatacccctatgtagttgtggaag
tttatgctaatattgtgtaactgatattaaacctaaatgttctgcctaccctgttggtat
aaagatatttttgagcagactgtaaacaagaaaaaaaaaatcatgcattcttagcaaaatt
gcctagtatgttaatttgctcaaaatacaatgtttgattttatgcactttgtcgctatta
acatcctttttttcatgtagatttcaataattgagtaattttagaagcattattttagga
atatatagttgtcacagtaaatatcttgttttttctatgtacattgtacaaattttttcat
tccttttgctctttgtggttggatctaacactaactgtattgttttgttacatcaaataa
acatcttctgtggaaaaaaaaaaaaaaaaaaaa
```

Figure 4
A) Regulation of VEGF expression by doxycycline (Tet-On)
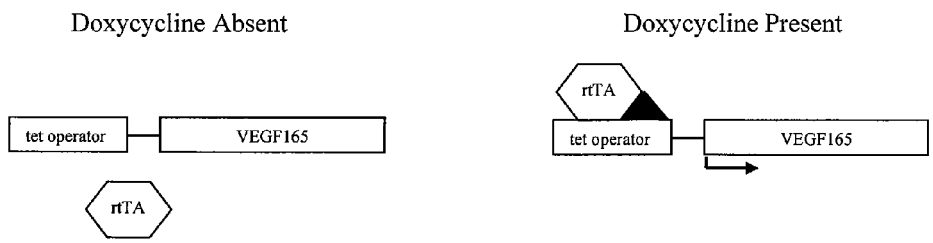
B) Regulation of Ang-1 expression by doxycycline (Tet-Off)
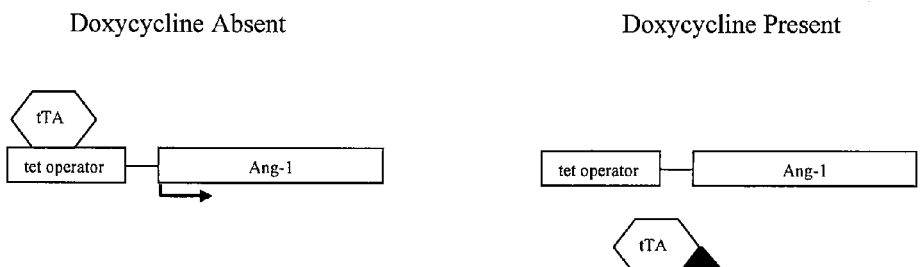

SEQUENCE LISTING

<160> NUMBER OF SEQ ID NOS: 4

<210> SEQ ID NO 1
<211> LENGTH: 658
<212> TYPE: DNA
<213> ORGANISM: Homo sapiens

<400> SEQUENCE: 1

```
ccatgaactt tctgctgtct tgggtgcatt ggagccttgc cttgctgctc tacctccacc      60
atgccaagtg gtcccaggct gcacccatgg cagaaggagg agggcagaat catcacgaag     120
tggtgaagtt catggatgtc tatcagcgca gctactgcca tccaatcgag accctggtgg     180
acatcttcca ggagtaccct gatgagatcg agtacatctt caagccatcc tgtgtgcccc     240
tgatgcgatg cggggctgc tgcaatgacg agggcctgga gtgtgtgccc actgaggagt     300
ccaacatcac catgcagatt atgcggatca aacctcacca aggccagcac ataggagaga     360
tgagcttcct acagcacaac aaatgtgaat gcagaccaaa gaaagataga gcaagacaag     420
aaaatccctg tgggccttgc tcagagcgga gaaagcattt gtttgtacaa gatccgcaga     480
cgtgtaaatg ttcctgcaaa aacacagact cgcgttgcaa ggcgaggcag cttgagttaa     540
acgaacgtac ttgcagatgt gacaagccga ggcggtgagc cgggcaggag gaaggagcct     600
ccctcagggt ttcgggaacc agatctctca ccaggaaaga ctgatacaga acgatcga      658
```

<210> SEQ ID NO 2
<211> LENGTH: 2149
<212> TYPE: DNA
<213> ORGANISM: Homo sapiens

<400> SEQUENCE: 2

```
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct ttgaggggga aagagtcaaa caaacaagca gttttacctg aaataaagaa     240
ctagttttag aggtcagaag aaaggagcaa gttttgcgag aggcacggaa ggagtgtgct     300
ggcagtacaa tgacagtttt cctttccttt gctttcctcg ctgccattct gactcacata     360
gggtgcagca atcagcgccg aagtccagaa acagtggga gaagatataa ccggattcaa      420
catgggcaat gtgcctacac tttcattctt ccagaacacg atggcaactg tcgtgagagt     480
acgacagacc agtacaacac aaacgctctg cagagagatg ctccacacgt ggaaccggat     540
ttctcttccc agaaacttca acatctggaa catgtgatgg aaaattatac tcagtggctg     600
caaaaacttg agaattacat tgtggaaaac atgaagtcgg agatggccca gatacagcag     660
aatgcagttc agaaccacac ggctaccatg ctggagatag aaccagcct cctctctcag      720 actgcagagc agaccagaaa gctgacagat gttgagaccc aggtactaaa tcaaacttct     780
cgacttgaga tacagctgct ggagaattca ttatccacct acaagctaga gaagcaactt     840
cttcaacaga caaatgaaat cttgaagatc catgaaaaaa acagtttatt agaacataaa     900
atcttagaaa tggaaggaaa acacaaggaa gagttggaca ccttaaagga agagaaagag     960
aaccttcaag gcttggttac tcgtcaaaca tatataatcc aggagctgga aaagcaatta    1020
aacagagcta ccaccaacaa cagtgtcctt cagaagcagc aactggagct gatggacaca    1080
gtccacaacc ttgtcaatct ttgcactaaa gaaggtgttt tactaaaggg aggaaaaaga    1140
gaggaagaga aaccatttag agactgtgca gatgtatatc aagctggttt taataaaagt    1200
ggaatctaca ctatttatat taataatatg ccagaaccca aaaggtgtt ttgcaatatg     1260 gatgtcaatg ggggaggttg gactgtaata caacatcgtg aagatggaag tctagatttc    1320
caaagaggct ggaaggaata taaaatgggt tttggaaatc cctccggtga atattggctg    1380
gggaatgagt ttattttgc cattaccagt cagaggcagt acatgctaag aattgagtta    1440
atggactggg aagggaaccg agcctattca cagtatgaca gattccacat aggaaatgaa    1500
aagcaaaact ataggttgta tttaaaaggt cacactggga cagcaggaaa acagagcagc    1560
ctgatcttac acggtgctga tttcagcact aaagatgctg ataatgacaa ctgtatgtgc    1620
aaatgtgccc tcatgttaac aggaggatgg tggtttgatg cttgtggccc ctccaatcta    1680
aatggaatgt tctatactgc gggacaaaac catggaaaac tgaatgggat aaagtggcac    1740
tacttcaaag gcccagttac tcccttacgt tccacaacta tgatgattcg accttttagat    1800 tttttgaaagc gcaatgtcag aagcgattat gaaagcaaca agaaatccg gagaagctgc    1860 caggtgagaa actgttttgaa aacttcagaa gcaaacaata ttgtctccct tccagcaata    1920
agtggtagtt atgtgaagtc accaaggttc ttgaccgtga atctggagcc gtttgagttc    1980
acaagagtct ctactggggg tgacagtgct cacgtggctc gactatagaa aactccactg    2040
actgtcgggc tttaaaaagg gaagaaactg ctgagcttgc tgtgcttcaa actactactg    2100
gaccttattt tggaactatg gtagccagat gataaatatg gttaatttc                2149
```

<210> SEQ ID NO 3
<211> LENGTH: 3180
<212> TYPE: DNA
<213> ORGANISM: Homo sapiens

<400> SEQUENCE: 3

| | | | | | |
|---|---|---|---|---|---|
| cacgaggcag | cactctcttc | gtcgcttcgg | ccagtgtgtc | gggctgggcc | ctgacaagcc | 60 |
| acctgaggag | aggctcggag | ccgggcccgg | accccggcga | ttgccgcccg | cttctctcta | 120 |
| gtctcacgag | gggtttcccg | cctcgcaccc | ccacctctgg | acttgccttt | ccttctcttc | 180 |
| tccgcgtgtg | gagggagcca | gcgcttaggc | cggagcgagc | ctgggggccg | cccgccgtga | 240 |
| agacatcgcg | gggaccgatt | caccatggag | ggcgccggcg | gcgcgaacga | caagaaaaag | 300 |
| ataagttctg | aacgtcgaaa | agaaaagtct | cgagatgcag | ccagatctcg | gcgaagtaaa | 360 |
| gaatctgaag | ttttttatga | gcttgctcat | cagttgccac | ttccacataa | tgtgagttcg | 420 |
| catcttgata | aggcctctgt | gatgaggctt | accatcagct | atttgcgtgt | gaggaaactt | 480 |
| ctggatgctg | gtgatttgga | tattgaagat | gacatgaaag | cacagatgaa | ttgcttttat | 540 |
| ttgaaagcct | tggatggttt | tgttatggtt | ctcacagatg | atggtgacat | gatttacatt | 600 |
| tctgataatg | tgaacaaata | catgggatta | actcagtttg | aactaactgg | acacagtgtg | 660 |
| tttgatttta | ctcatccatg | tgaccatgag | gaaatgagag | aaatgcttac | acacagaaat | 720 |
| ggccttgtga | aaagggtaa | agaacaaaac | acacagcgaa | gctttttttct | cagaatgaag | 780 |
| tgtaccctaa | ctagccgagg | aagaactatg | aacataaagt | ctgcaacatg | gaaggtattg | 840 |
| cactgcacag | gccacattca | cgtatatgat | accaacagta | accaacctca | gtgtgggtat | 900 |
| aagaaaccac | ctatgacctg | cttggtgctg | atttgtgaac | ccattcctca | cccatcaaat | 960 |
| attgaaattc | ctttagatag | caagactttc | ctcagtcgac | acagcctgga | tatgaaattt | 1020 |
| tcttattgtg | atgaaagaat | taccgaattg | atgggatatg | agccagaaga | acttttaggc | 1080 |
| cgctcaattt | atgaatatta | tcatgctttg | gactctgatc | atctgaccaa | aactcatcat | 1140 |
| gatatgttta | ctaaaggaca | agtcaccaca | ggacagtaca | ggatgcttgc | caaaagaggt | 1200 |
| ggatatgtct | gggttgaaac | tcaagcaact | gtcatatata | acaccaagaa | ttctcaacca | 1260 |
| cagtgcattg | tatgtgtgaa | ttacgttgtg | agtggtatta | ttcagcacga | cttgattttc | 1320 |
| tcccttcaac | aaacagaatg | tgtccttaaa | ccggttgaat | cttcagatat | gaaaatgact | 1380 |
| cagctattca | ccaaagttga | atcagaagat | acaagtagcc | tctttgacaa | acttaagaag | 1440 |
| gaacctgatg | ctttaacttt | gctggcccca | gccgctggag | acacaatcat | atctttagat | 1500 |
| tttggcagca | acgacacaga | aactgatgac | cagcaacttg | aggaagtacc | attatataat | 1560 |
| gatgtaatgc | tccccctcacc | caacgaaaaa | ttacagaata | taaatttggc | aatgtctcca | 1620 |
| ttacccaccg | ctgaaacgcc | aaagccactt | cgaagtagtg | ctgaccctgc | actcaatcaa | 1680 |
| gaagttgcat | taaaattaga | accaaatcca | gagtcactgg | aactttcttt | taccatgccc | 1740 |
| cagattcagg | atcagacacc | tagtccttcc | gatggaagca | ctagacaaag | ttcacctgag | 1800 |
| cctaatagtc | ccagtgaata | ttgttttttat | gtggatagta | tatggtcaa | tgaattcaag | 1860 |
| ttggaattgg | tagaaaaact | ttttgctgaa | gacacagaag | caagaacccc | attttctact | 1920 |
| caggacacag | atttagactt | ggagatgtta | gctccctata | tcccaatgga | tgatgacttc | 1980 |
| cagttacgtt | ccttcgatca | gttgtcacca | ttagaaagca | gttccgcaag | ccctgaaagc | 2040 |
| gcaagtcctc | aaagcacagt | tacagtattc | cagcagactc | aaatacaaga | acctactgct | 2100 |
| aatgccacca | ctaccactgc | caccactgat | gaattaaaaa | cagtgacaaa | agaccgtatg | 2160 |

```
gaagacatta aaatattgat tgcatctcca tctcctaccc acatacataa agaaactact    2220
agtgccacat catcaccata tagagatact caaagtcgga cagcctcacc aaacagagca    2280
ggaaaaggag tcatagaaca gacagaaaaa tctcatccaa gaagccctaa cgtgttatct    2340
gtcgctttga gtcaaagaac tacagttcct gaggaagaac taaatccaaa gatactagct    2400
ttgcagaatg ctcagagaaa gcgaaaaatg gaacatgatg gttcactttt tcaagcagta    2460
ggaattggaa cattattaca gcagccagac gatcatgcag ctactacatc actttcttgg    2520
aaacgtgtaa aaggatgcaa atctagtgaa cagaatggaa tggagcaaaa gacaattatt    2580
ttaataccct ctgatttagc atgtagactg ctggggcaat caatggatga aagtggatta    2640
ccacagctga ccagttatga ttgtgaagtt aatgctccta tacaaggcag cagaaaccta    2700
ctgcagggtg aagaattact cagagctttg gatcaagtta actgagcttt ttcttaattt    2760 cattccttt tttggacact ggtggctcac tacctaaagc agtctattta tattttctac    2820
atctaatttt agaagcctgg ctacaatact gcacaaactt ggttagttca attttttgatc    2880 cccttctac ttaatttaca ttaatgctct tttttagtat gttctttaat gctggatcac    2940
agacagctca ttttctcagt tttttggtat ttaaaccatt gcattgcagt agcatcattt    3000
taaaaaatgc accttttat ttatttattt ttggctaggg agtttatccc tttttcgaat    3060 tattttaag aagatgccaa tataatttt gtaagaaggc agtaaccttt catcatgatc    3120
ataggcagtt gaaaaatttt tacaccttt ttttcacatt ttacataaat aataatgctt    3180

<210> SEQ ID NO 4
<211> LENGTH: 753
<212> TYPE: DNA
<213> ORGANISM: Homo sapiens

<400> SEQUENCE: 4
tgccagcagt acgtggtagc cacaattgca caatatattt tcttaaaaaa taccagcagt      60
tactcatgga atatattctg cgtttataaa actagttttt aagaagaaat ttttttttggc     120 ctatgaaatt gttaaacctg gaacatgaca ttgttaatca tataataatg attcttaaat     180
gctgtatggt ttattattta aatgggtaaa gccatttaca taatatagaa agatatgcat     240
atatctagaa ggtatgtggc atttatttgg ataaaattct caattcagag aaatcatctg     300
atgtttctat agtcactttg ccagctcaaa agaaaacaat accctatgta gttgtggaag     360
tttatgctaa tattgtgtaa ctgatattaa acctaaatgt tctgcctacc ctgttggtat     420
aaagatattt tgagcagact gtaaacaaga aaaaaaaaat catgcattct tagcaaaatt     480
gcctagtatg ttaatttgct caaaatacaa tgtttgattt tatgcacttt gtcgctatta     540
acatcctttt tttcatgtag atttcaataa ttgagtaatt ttagaagcat tattttagga     600
atatatagtt gtcacagtaa atatcttgtt ttttctatgt acattgtaca aatttttcat     660
tccttttgct ctttgtggtt ggatctaaca ctaactgtat tgtttttgtta catcaaataa     720 acatcttctg tggaaaaaaa aaaaaaaaaa aaa                                  753
```

KERATINOCYTES EXPRESSING EXOGENOUS ANGIOGENIC GROWTH FACTORS

CROSS REFERENCE TO RELATED APPLICATIONS

This application is a continuation of U.S. patent application Ser. No. 10/425,784, filed Apr. 29, 2003, (allowed), which claims the benefit of provisional application 60/376,488, filed Apr. 30, 2002, both of which are incorporated herein by reference in their entirety.

FIELD OF THE INVENTION

The present invention relates to in vitro cultured skin tissue, and in particular to cultured skin tissue comprising exogenous genes encoding angiogenic growth factors.

BACKGROUND OF THE INVENTION

Skin loss due to burns and ulcers is a major medical problem. In the United States, it is estimated that 1.25 million people need medical care for burns each year. Approximately 51,000 people are hospitalized for burns and 13,000 require skin grafts. Of these, 1,500 are severely burned and require extensive grafting. With respect to skin ulcers, it is estimated that 800,000 diabetics in the United States suffer from chronic, non-healing diabetic foot ulcers. Infections of some of these skin ulcers result in 50,000 amputations each year. In addition to diabetic ulcers, new products are needed for venous ulcers, and pressure ulcers (bedsores).

Several products employ bioengineered skin tissue, some of which include cultured keratinocytes with or without a dermal component. In patients with large total body surface area full-thickness burns, the burned skin is first removed to reduce toxicity from degradation of the necrotic tissue and to reduce microbial growth in the wound. Excised wounds are covered temporarily with cadaver skin to reduce fluid loss and infection (Boyce et al., J. Burn Care Rehab. 20(6):453-461 (1999)). The culture methods of Rheinwald and Green have allowed sheets of autologous keratinocytes to be used in the clinic since 1985. However the lack of a dermal component in some of these products, e.g., Genzyme's Epicel, limits their utility. Other products consist of only a dermal analog, e.g., Advanced Tissue Science's Transcyte and Dermagraft and LifeCell's Alloderm. These products currently are not as effective as split thickness autologous grafts, which remain the method of choice for the treatment of full-thickness skin loss. However autologous grafts may not be possible in patients with extensive burns and even in other patients create wound-healing problems at the autograft donor site including opportunities for infection and the generation of functional or cosmetic defects.

The organotypic culture technique for normal keratinocytes has fostered the recent development of cultured skin tissue for the treatment of burns and skin wounds. Composite grafts consist of keratinocytes seeded onto dermal analogs, e.g., a fibroblast-contracted collagen in the Apligraf product from Organogenesis. Composite grafts, however, are reportedly more fragile and slower to revascularize. The use of cultured skin tissue for burn or wound therapy can therefore be limited by poor vascularization of the graft. In autografts, vascularization occurs by inosculation and neovascularization. Inosculation proceeds by the joining of capillaries in the wound bed to ends of the severed vessels in the dermis of the graft. This is the primary mechanism of early vascularization. Vascularization of composite grafts takes longer than an autograft because it relies only on neovascularization. The poor vascularization of composite grafts leads to graft ischemia and a delayed time to successful engraftment.

Because of the limitations of current bio-engineered tissues, there is a great deal of opportunity for improved products for the treatment of burns and skin wounds. Clearly, a great need exists for cultured skin tissue having improved properties for transplantation.

SUMMARY OF THE INVENTION

The present invention relates to in vitro cultured skin tissue, and in particular to cultured skin tissue comprising exogenous genes encoding angiogenic growth factors. Accordingly, in some embodiments, the present invention provides a composition comprising keratinocytes, the keratinocytes comprising at least one exogenous angiogenic factor or activator operably linked to an inducible promoter. The present invention is not limited to any particular source of keratinocytes. Indeed, the use of a variety of sources of keratinocytes is contemplated. In some embodiments, the keratinocytes are selected from the group consisting of primary keratinocytes and immortalized keratinocytes. In some preferred embodiments, the immortalized keratinocytes are NIKS cells. In other embodiments, the compositions further comprise a dermal equivalent. In some preferred embodiments, the dermal equivalent comprises collagen and fibroblasts. In still other embodiments, the keratinocytes are stratified, thereby forming cultured skin tissue. In some preferred embodiments, the skin tissue is stratified into squamous epithelia.

The present invention is not limited to the expression of any particular angiogenic factor. Indeed, the use of a variety of angiogenic factors or activators is contemplated. In some preferred embodiments, the angiogenic factor is selected from the group consisting of a VEGF gene, an angiopoietin gene, and a HIF1α gene. In other preferred embodiments, the VEGF gene is VEGF-A. In other preferred embodiments, the VEGF-A gene is encoded by SEQ ID NO:1 or sequences that hybridize to SEQ ID NO:1 under conditions of low stringency.

In still other preferred embodiments, the angiopoietin gene is angiopoietin-1. In further preferred embodiments, the angiopoietin-1 gene is encoded by SEQ ID NO:2 or sequences that hybridize to SEQ ID NO:2 under conditions of low stringency. In further embodiments, the angiogenic activator is HIF1α. In further preferred embodiments, the HIF-1α gene is encoded by SEQ ID NO:3 or sequences that hybridize to SEQ ID NO:3 under conditions of low stringency. In some other embodiments, the keratinocytes are transfected with combinations of VEGF-A, ANG-1, and HIF-1. The present invention is not limited to the use of any particular inducible promoter. Indeed, the use of a variety of inducible promoters is contemplated, including, but not limited to the Tet-responsive promoter.

In some embodiments, the present invention provides methods of treatment comprising providing a subject in need of graft and a graft, wherein the graft comprises keratinocytes comprising at least one exogenous angiogenic factor operably linked to an inducible promoter; and grafting the graft onto the subject under conditions such that the graft vascularizes. The present invention is not limited to any particular source of keratinocytes. Indeed, the use of a variety of sources of keratinocytes is contemplated. In some embodiments, the keratinocytes are selected from the group consisting of primary keratinocytes and immortalized keratinocytes. In some preferred embodiments, the immortalized keratinocytes are NIKS cells. In other embodiments, the compositions further comprise a dermal equivalent. In some preferred embodiments, the dermal equivalent comprises collagen and fibroblasts. In still other embodiments, the keratinocytes are stratified, thereby forming cultured skin tissue. In some preferred embodiments, the skin tissue is stratified into squamous epithelia.

The present invention is not limited to the expression of any particular angiogenic factor. Indeed, the use of a variety of angiogenic factors or activators is contemplated. In some preferred embodiments, the angiogenic factor is selected from the group consisting of a VEGF gene, an angiopoietin gene and a HIF1α gene. In other preferred embodiments, the VEGF gene is VEGF-A. In other preferred embodiments, the VEGF-A gene is encoded by SEQ ID NO:1 or sequences that hybridize to SEQ ID NO:1 under conditions of low stringency.

In still other preferred embodiments, the angiopoietin gene is angiopoietin-1. In further preferred embodiments, the angiopoietin-1 gene is encoded by SEQ ID NO:2 or sequences that hybridize to SEQ ID NO:2 under conditions of low stringency. In further embodiments, the angiogenic activator is HIF-1α. In further preferred embodiments, the HIF-1α gene is encoded by SEQ ID NO:3 or sequences that hybridize to SEQ ID NO:3 under conditions of low stringency. In some other embodiments, the keratinocytes are transfected with combinations of VEGF-A, ANG-1, and HIF-1α. The present invention is not limited to the use of any particular inducible promoter. Indeed, the use of a variety of inducible promoters is contemplated, including, but not limited to the Tet-responsive promoter. In some further preferred embodiments, vascularization is induced by topical administration of an agent such as doxycycline.

In other embodiments, a skin graft composition comprising at least first and second sub-populations of keratinocytes, wherein the first subpopulation of keratinocytes is transfected with a first exogenous angiogenic factor and the second sub-population is transfected with a second exogenous angiogenic factor. In some preferred embodiments, the first angiogenic factor is encoded by SEQ ID NO:1 or sequences that bind to SEQ ID NO:1 under conditions of low stringency. In still other preferred embodiments, the second angiogenic factor is encoded by SEQ ID NO:2 or sequences that bind to SEQ ID NO:2 under conditions of low stringency. The first or second angiogenic factor can also be an angiogenic activator such as HIF-1α.

DESCRIPTION OF THE FIGURES

FIG. 1 provides the sequence for VEGF-A (SEQ ID NO:1).
FIG. 2 provides the sequence for ANG-1 (SEQ ID NO:2).
FIGS. 3a and 3b provide the sequence for HIF-1α (SEQ ID NO:3).
FIG. 4 provides a schematic depiction of inducible expression of an angiogenic factor.

DEFINITIONS

As used herein, the terms "skin equivalent" and "skin substitute" are used interchangeably to refer to an in vitro derived culture of keratinocytes that has stratified into squamous epithelia. Typically, cultured skin tissue is produced by organotypic culture.

As used herein, the term "organotypic" culture refers to a three-dimensional tissue culture where cultured cells are used to reconstruct a tissue or organ in vitro.

As used herein, the term "NIKS cells" refers to cells having the characteristics of the cells deposited as cell line ATCC CRL-12191.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term response, when used in reference to an assay, refers to the generation of a detectable signal (e.g., accumulation of reporter protein, increase in ion concentration, accumulation of a detectable chemical product).

As used herein, the term reporter gene refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

The term "gene" refers to a nucleic acid (e.g., DNA) sequence that comprises coding sequences necessary for the production of a polypeptide or precursor (e.g., VEGF or ANG-1). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "VEGF-A gene" includes the full-length VEGF-A nucleotide sequence (e.g., contained in SEQ ID NO:1). However, it is also intended that the term encompass fragments of the VEGF-A sequence, as well as other domains within the full-length VEGF-A nucleotide sequence. Accordingly, the term "VEGF-A gene" encompasses VEGF-A homologs containing substitution, addition, and deletion mutations and splice variants of VEGF-A. Furthermore, the terms "VEGF-A nucleotide sequence" or "VEGF-A polynucleotide sequence" encompasses DNA, cDNA, and RNA (e.g., mRNA) sequences.

The term "ANG-1 gene" includes the full-length angiopoietin-1 (ANG-1) nucleotide sequence (e.g., contained in SEQ ID NO:2). However, it is also intended that the term encompass fragments of the ANG-1 sequence, as well as other domains within the full-length ANG-1 nucleotide sequence. Accordingly, the term "ANG-1 gene" encompasses ANG-1 homologs containing substitution, addition, and deletion mutations and splice variants of ANG-1. Furthermore, the terms "ANG-1 nucleotide sequence" or "ANG-1 polynucleotide sequence" encompasses DNA, cDNA, and RNA (e.g., mRNA) sequences.

The term "HIF-1α gene" includes the full-length hypoxia-inducing factor (HIF-1α) nucleotide sequence (e.g., contained in SEQ ID NO:3). However, it is also intended that the term encompass fragments of the HIF-1α sequence, as well as other domains within the full-length HIF-1α nucleotide sequence. Accordingly, the term "HIF-1α gene" encompasses HIF-1α homologs containing substitution, addition, and deletion mutations and splice variants of HIF-1α. Furthermore, the terms "HIF-1α nucleotide sequence" or "HIF-1α polynucleotide sequence" encompasses DNA, cDNA, and RNA (e.g., mRNA) sequences.

Where amino acid sequence is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, the sequence "5'-A-G-T-3'" is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described below.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as, greater than, or less than the efficiency of substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% G+C)$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42 C in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50× Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol.*

*Biol.* 48:443 (1970)], by the search for similarity method of Pearson and Lipman [Pearson and Lipman, *Proc. Natl. Acad. Sci.* (*U.S.A.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., VEGF and ANG-1).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, the term "recombinant DNA molecule" refers to a DNA molecule that is comprised of segments of DNA joined together by means of molecular biological techniques.

As used herein, the term "vector" refers to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the VEGF mRNA-specific signal observed on Northern blots). The amount of mRNA present in the band corresponding in size to the correctly spliced VEGF or ANG-1 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics. The terms "transfection" and "transformation" may be used interchangeably.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, *Virol.*, 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding VEGF, ANG-1, or HIF-1α (e.g., SEQ ID NOs:1, 2 or 3) or fragments thereof may be employed as hybridization probes. In this case, the VEGF, ANG-1, or HIF-1α encoding polynucleotide sequences are typically employed in an aqueous solution containing salts (e.g., NaCl), detergents (e.g., SDS), and other components (e.g., Denhardt's solution, dry milk, salmon sperm DNA, etc.).

DESCRIPTION OF THE INVENTION

The present invention relates to in vitro cultured skin tissue, and in particular to cultured skin tissue comprising exogenous genes encoding angiogenic growth factors.

Human skin is composed of a dermal layer containing fibroblasts embedded in an extracellular protein matrix and an epidermal layer, consisting primarily of keratinocytes that differentiate to form the outermost, impermeable skin layer. Differentiated keratinocytes are continuously lost from the surface and replaced by the proliferation of basal keratinocytes. The rate at which a basal cell initiates and completes its differentiation program appears to be tightly regulated, although the molecular controls for such regulation are ill defined. In vivo, the final stages of the terminal differentiation process are characterized by numerous changes including filaggrin-mediated keratin intermediate filament bundling, and release of lipids from membrane-coating granules into the intercellular space. The cornified envelope (CE), another terminal differentiation structure consisting of several proteins that are covalently cross-linked by the action of calcium-dependent transglutaminases, is also formed in differentiating keratinocytes. In the epidermis, keratinocytes lose intracellular organelles and enucleate in the upper layers of the tissue, forming a "dead shell" with high tensile strength. Molecular mechanisms that govern keratinocyte enucleation and terminal differentiation are poorly understood.

Full stratification and histological differentiation of normal keratinocytes can be achieved by the use of three-dimensional organotypic culture methods (See, e.g., Bell et al., Proc. Natl. Acad. Sci. USA 76:1274-78 (1979); Parenteau et al., Cytotechnology 9:163-71 (1992)). Keratinocytes grown on the surface of collagen gels containing dermal fibroblasts can generate specialized structures, such as the basement membrane and hemidesmosomes, which are characteristic of the normal tissue architecture of stratified squamous epithelia.

The present invention provides cultured skin tissue comprising exogenous genes encoding angiogenic growth factors. It is contemplated that this cultured skin tissue has improved vascularization properties as compared to cultured skin tissue lacking these exogenous genes. For convenience, the description of the invention is presented in the following sections: A) Sources of Keratinocytes and Other Cells for Creating Cultured Skin Tissue; B) Expression of Exogenous Angiogenic Growth Factors in Cultured Skin Tissue; and C) Uses of Cultured Skin Tissue.

A. Sources of Keratinocytes and Other Cells for Creating Cultured Skin Tissue

Generally, any source of cells or cell line that can stratify into squamous epithelia are useful in the present invention. Accordingly, the present invention is not limited to the use of any particular source of cells that are capable of differentiating into squamous epithelia. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cavaderic donors (Auger et al., In Vitro Cell. Dev. Biol.—Animal 36:96-103; U.S. Pat. Nos. 5,968,546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucamp et al., J. cell. Boil. 106:761-771 (1988)); and NIKS cells (Cell line BC-1-Ep/SL; U.S. Pat. No. 5,989,837, incorporated herein by reference; ATCC CRL-12191). Each of these cell lines can be cultured or genetically modified as described below.

In preferred embodiments, NIKS cells are utilized. The discovery of a novel human keratinocyte cell line (normal immortalized keratinocytes or NIKS) provides an opportunity to genetically engineer human keratinocytes for grafts and new in vitro testing methods. A unique advantage of the NIKS cells is that they are a consistent source of genetically-uniform, pathogen-free human keratinocytes. For this reason, they are useful for the application of genetic engineering and genomic gene expression approaches to provide cultured skin tissue with properties similar to human skin. Such systems will provide an important alternative to the use of animals for testing compounds and formulations. The NIKS keratinocyte cell line, identified and characterized at the University of Wisconsin, is nontumorigenic and exhibits normal growth and differentiation both in monolayer and organotypic culture. NIKS cells form fully stratified skin tissue in culture. These cultures are indistinguishable by all criteria tested thus far from organotypic cultures formed from primary human keratinocytes. Unlike primary cells however, the immortalized NIKS cells will continue to proliferate indefinitely. This provides an opportunity to genetically manipulate the cells and isolate new clones of cells with new useful properties (Allen-Hoffmann et al., J. Invest. Dermatol., 114(3): 444-455 (2000)).

The NIKS cell line is useful for in vitro assays because it provides a consistent source of genetically identical human keratinocytes. The NIKS cells arose from the BC-1-Ep strain of human neonatal foreskin keratinocytes isolated from an apparently normal male infant. In early passages, the BC-1-Ep cells exhibited no morphological or growth characteristics that were atypical for cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3 \times 10^5$ cells per 100-mm dish and passaged at weekly intervals (approximately a 1:25 split). By passage 15, most keratinocytes in the population appeared senescent as judged by the presence of numerous abortive colonies that exhibited large, flat cells. However, at passage 16, keratinocytes exhibiting a small cell size were evident. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that survived senescence were serially cultivated at a density of $3 \times 10^5$ cells per 100-mm dish. Typically the cultures reached a cell density of approximately 8×10⁶ cells within 7 days. This stable rate of cell growth was maintained through at least 59 passages, demonstrating that the cells had achieved immortality. The keratinocytes that emerged from the original senescencing population were originally designated BC-1-Ep/Spontaneous Line and are now termed NIKS. The NIKS™ cell line has been extensively screened for the presence of specific viral pathogens, including HIV-1, HIV-2, HTLV-1, HTLV-2, HBV, HCV, EBV, CMV, HPV and B19 human parvovirus. None of these viruses were detected. In addition, examination of mice and embryonated eggs inoculated with NIKS™ cell extracts demonstrates that NIKS™ keratinocytes are free of unidentified viral adventitious agents. The NIKS™ cell line is also free of mycoplasma contamination as determined by Hoechst and broth culture.

Chromosomal analysis was performed on the parental BC-1-Ep cells at passage 3 and NIKS cells at passages 31 and 54. The parental BC-1-Ep cells have a normal chromosomal complement of 46, XY. At passage 31, all NIKS cells contained 47 chromosomes with an extra isochromosome of the long arm of chromosome 8. No other gross chromosomal abnormalities or marker chromosomes were detected. At passage 54, the only cytogenetic abnormality in NIKS cells was the presence of isochromosome 8. Thus, NIKS cells exhibit a stable, near-diploid karyotype.

The DNA fingerprints for the NIKS cell line and the BC-1-Ep keratinocytes are identical at all twelve loci analyzed. The odds of the NIKS cell line having the parental BC-1-Ep DNA fingerprint by random chance is $4 \times 10^{-16}$. The DNA fingerprints from three different sources of human keratinocytes, ED-1-Ep, SCC4 and SCC13y are different from the BC-1-Ep pattern. The data from the DNA fingerprint analysis of the NIKS cell line proves it arose from the parental BC-1-Ep cells. This data also shows that keratinocytes isolated from other humans, ED-1-Ep, SCC4, and SCC13y, are unrelated to the BC-1-Ep cells or each other. The NIKS DNA fingerprint data provides an unequivocal way to identify the NIKS cell line.

Loss of p53 function is associated with an enhanced proliferative potential and increased frequency of immortality in cultured cells. The sequence of p53 in the NIKS cells is identical to published p53 sequences (GenBank accession number: M14695). In humans, p53 exists in two predominant polymorphic forms distinguished by the amino acid at codon 72. Both alleles of p53 in the NIKS cells are wild-type and have the sequence CGC at codon 72, which codes for an arginine. The other common form of p53 has a proline at this position. The entire sequence of p53 in the NIKS cells is identical to the BC-1-Ep progenitor cells. Rb was also found to be wild-type in NIKS cells.

Anchorage-independent growth is highly correlated to tumorigenicity in vivo. For this reason, the anchorage-independent growth characteristics of NIKS cells in agar or methylcellulose-containing medium was investigated. After 4 weeks in either agar- or methylcellulose-containing medium, NIKS cells remained as single cells. The assays were continued for a total of 8 weeks to detect slow growing variants of the NIKS cells. None were observed.

To determine the tumorigenicity of the parental BC-1-Ep keratinocytes and the immortal NIKS keratinocyte cell line, cells were injected into the flanks of athymic nude mice. The human squamous cell carcinoma cell line, SCC4, was used as a positive control for tumor production in these animals. The injection of samples was designed such that animals received SCC4 cells in one flank and either the parental BC-1-Ep keratinocytes or the NIKS cells in the opposite flank. This injection strategy eliminated animal to animal variation in tumor production and confirmed that the mice would support vigorous growth of tumorigenic cells. Neither the parental BC-1-Ep keratinocytes (passage 6) nor the NIKS keratinocytes (passage 35) produced tumors in athymic nude mice.

NIKS cells were analyzed for the ability to undergo differentiation in both submerged culture and organotypic culture. For cells in submerged culture, a marker of squamous differentiation, the formation cornified envelopes (CE) was monitored. In cultured human keratinocytes, early stages of CE assembly result in the formation of an immature structure composed of involucrin, cystatin-α and other proteins, which represent the innermost third of the mature CE. CE formation in the parental and the NIKS keratinocytes was examined. Less than 2% of the keratinocytes from the adherent BC-1-Ep cells or the NIKS cell line produce CEs. This finding is consistent with previous studies demonstrating that actively growing, subconfluent keratinocytes produce less than 5% CEs. Many aspects of terminal differentiation, including differential expression of keratins and CE formation can be triggered in vitro by loss of keratinocyte cell-cell and cell-substratum adhesion. To determine whether the NIKS cell line is capable of producing CEs when induced to differentiate, the cells were removed from submerged culture and suspended for 24 hours in medium made semi-solid with methylcellulose. The NIKS keratinocytes produced as many as and usually more CEs than the parental keratinocytes. These findings demonstrate that the NIKS keratinocytes are not defective in their ability to initiate the formation of this cell type-specific differentiation structure.

To confirm that the NIKS keratinocytes can undergo squamous differentiation, the cells were cultivated in organotypic culture. Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy, there are striking differences between the architecture of the multilayered sheets formed in tissue culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the parental cells and the NIKS cells. The appearance of flattened squamous cells is evident in the upper layers of keratinocytes and demonstrates that stratification has occurred in the organotypic cultures. In the uppermost part of the organotypic cultures the enucleated squames peel off the top of the culture. To date, no histological differences in differentiation at the light microscope level between the parental keratinocytes and the NIKS keratinocyte cell line grown in organotypic culture have been observed To observe more detailed characteristics of the parental (passage 5) and NIKS (passage 38) organotypic cultures and to confirm the histological observations, samples were analyzed using electron microscopy. Parental cells and the immortalized human keratinocyte cell line, NIKS, were harvested after 15 days in organotypic culture and sectioned perpendicular to the basal layer to show the extent of stratification. Both the parental cells and the NIKS cell line undergo extensive stratification in organotypic culture and form structures that are characteristic of normal human epidermis. Abundant desmosomes are formed in organotypic cultures of parental cells and the NIKS cell line. The formation of a basal lamina and associated hemidesmosomes in the basal keratinocyte layers of both the parental cells and the cell line was also noted. Hemidesmosomes are specialized structures that increase adhesion of the keratinocytes to the basal lamina and help maintain the integrity and strength of the tissue. The presence of these structures was especially evident in areas where the parental cells or the NIKS cells had attached directly to the mesh support. These findings are consistent with earlier ultrastructural findings using human foreskin keratinocytes cultured on a fibroblast-containing nylon mesh. Analysis at both the light and electron microscopic levels demonstrate that the NIKS cell line in organotypic culture can stratify, differentiate, and form structures such as desmosomes, basal lamina, and hemidesmosomes found in normal human epidermis.

B. Expression of Exogenous Angiogenic Growth Factors in Cultured Skin Tissue

In preferred embodiments of the present invention, the keratinocytes used to form cultured skin tissue comprise at least one angiogenic growth factor. In some preferred embodiments, the angiogenic growth factor is a member of the VEGF family (e.g., VEGF-A, -B, -C, -D, and PIGF). In other preferred embodiments, the angiogenic growth factor is angiopoietin or an angiopoietin related protein.

Five closely related proteins (VEGF-A, VEGF-B, VEGF-C, VEGF-D and PIGF) comprise the VEGF family (Eriksson and Alitalo, Curr Top Microbiol Immunol 237:41-57. (1999), Persico, et al., Curr Top Microbiol Immunol 237:31-40. (1999)). While most of these factors appear to play very specific roles in vascular or lymphatic development (Olofsson, et al., Curr Opin Biotechnol 10:528-35. (1999), Carmeliet, Nat Med 6:389-95. (2000), Bellomo, et al., Circ Res 86:E29-35. (2000)), VEGF-A has potent angiogenic activities and is expressed during angiogenesis induced by a wide variety of stimuli.

VEGF-A was initially identified in the conditioned medium of bovine pituitary folliculostellate cells and tumors (Senger, et al., Science 219:983-5. (1983), Ferrara and Henzel, Biochem Biophys Res Commun 161:851-8. (1989), Ferrara, et al., Methods Enzymol 198:391-405. (1991)). VEGF-A is a dimeric glycoprotein that is a potent mitogen for microvascular endothelial cells in vitro (Detmar, et al., J Invest Dermatol 105:44-50. (1995)) and exhibits angiogenic activity in vivo. Four VEGF-A isoforms of 121, 165, 189, and 206 amino acids are expressed from the VEGF-A gene by alternative splicing (Houck, et al., Mol Endocrinol 5:1806-14. (1991)). All four isoforms contain an N-terminal signal peptide, but the two largest forms contain a highly basic 24 amino acid domain that prevents their efficient secretion. The secreted VEGF-A homodimers and heterodimers bind to three transmembrane tyrosine kinases, VEGFR-1 (Flt-1), VEGFR-2 (KDR), and VEGFR-3 (Flt-3), which are expressed exclusively on the surface of microvascular endothelial cells (Yancopoulos, et al., Nature 407:242-8. (2000)). This highly restricted expression of the VEGF receptors appears to be responsible for the highly selective actions of VEGF-A for endothelial cells. Signaling through VEGFR-2 appears to be responsible for most of the proliferative and permeability effects of VEGF (Shalaby, et al., Nature 376:62-6. (1995)), while binding of VEGF-A to VEGFR-1 may act to inhibit signaling through VEGFR-2 (Fong, et al., Nature 376:66-70. (1995)).

The process of angiogenesis involves local destabilization of the quiescent vasculature, reorganization and proliferation of endothelial cells to form new blood vessels, and the maturation of these nascent blood vessels into a stable vascular network. VEGF-A is thought to play an early role in angiogenesis by promoting the migration and proliferation of microvascular endothelial cells. In addition, VEGF-A promotes vascular hyperpermeability in response to inflammation and tissue ischemia. VEGF-A is required for embryonic vascular development and loss of even one VEGF-A allele in mice results in embryonic lethality due to poorly formed vasculature (Carmeliet, et al., Nature 380:435-9. (1996), Ferrara, et al., Nature 380:439-42. (1996)). In the adult, VEGF-A is expressed primarily in sites of vascular remodeling, such as the ovary and endometrium (Maisonpierre, et al., Science 277:55-60. (1997), Moller, et al., Mol Hum Reprod 7:65-72. (2001)).

VEGF-A expression is also associated with pathological conditions involving angiogenesis, including inflammation, wound healing (Brown, et al., J Exp Med 176:1375-9. (1992)), psoriasis (Detmar, et al., J Exp Med 180:1141-6. (1994)), and tumor vascularization (Shweiki, et al., Proc Natl Acad Sci USA 92:768-72. (1995)). Human keratinocytes express VEGF121, VEGF165, and VEGF189 during wound healing and the expression of these proteins in keratinocytes is induced by hypoxia (Brown, et al., J Exp Med 176:1375-9. (1992), Ballaun, et al., J Invest Dermatol 104:7-10. (1995), Detmar, et al., J Invest Dermatol 108:263-8. (1997)). VEGF-A expression during wound healing leads to increased angiogenesis and increased vascularization of the hypoxic tissue. The permeabilizing effects of VEGF-A lead to leakage of serum proteins and clotting, which facilitate the deposition of extracellular matrix components. VEGF-A stimulates the proliferation and migration of endothelial cells into the wound bed, resulting in increased angiogenesis. The importance of VEGF-A in wound healing is illustrated by the observation that reduced VEGF-A expression is correlated with impaired cutaneous wound healing in diabetic mice (Frank, et al., J Biol Chem 270:12607-13. (1995), Rivard, et al., Am J Pathol 154:355-63. (1999)).

The pivotal role of VEGF-A in angiogenesis is illustrated by enhanced vascularization of mice engineered to over-express VEGF-A. Targeted expression of VEGF-A to the skin of transgenic mice resulted in marked increases in blood vessel density, although the resulting vessels were hyperpermeable (Larcher, et al., Oncogene 17:303-11. (1998), Detmar, et al., J Invest Dermatol 111:1-6. (1998)). These observations indicated that VEGF-A expression alone leads to abnormal angiogenesis, and that other factors are required for normal angiogenesis. Although VEGF-A promotes the initial stages of angiogenesis, maturation and stability of the resulting vasculature requires the action of other angiogenic factors, notably the angiopoietins.

The angiopoietins were recently identified as ligands for the endothelial cell-specific Tie2 receptor (Maisonpierre, et al., Science 277:55-60. (1997), Davis, et al., Cell 87:1161-9. (1996)). While angiopoietin-1 (Ang-1) binds to and activates the tyrosine kinase activity of Tie2, the binding of angiopoietin-2 (Ang-2) to Tie2 does not result in its activation. The angiopoietins appear to work in concert with other angiogenic factors to modulate the stability of microvascular networks (Maisonpierre, et al., Science 277:55-60. (1997), Davis, et al., Cell 87:1161-9. (1996), Suri, et al., Cell 87:1171-80. (1996)). Angiopoietin-1 (Ang-1) is widely expressed in adult tissues and is thought to promote formation of mature blood vessels by enhancing the interactions between adjacent endothelial cells by the increasing the expression of PECAM-1 (Gamble, et al., Circ Res 87:603-7. (2000)). In contrast, Ang-2 is expressed primarily in areas undergoing vascular remodeling and is thought to promote vascular plasticity by locally suppressing the stabilizing influence of Ang-1 (Maisonpierre, et al., Science 277:55-60. (1997)). These observations have led to the hypothesis that Ang-1 and Ang-2 act in opposition to each other to mediate the plasticity of the microvascular network.

Loss of Ang-1 or the Tie2 receptor in mice leads to lethality and defective vascular development (Suri, et al., Cell 87:1171-80. (1996), Sato, et al., Nature 376:70-4. (1995)). Although the initial stages of angiogenesis proceed relatively normally, the subsequent maturation and stabilization of the embryonic vasculature fails to occur in Ang-1 or Tie2 mutant mice. This is consistent with observations that Ang-1 promotes stabilization of blood vessels by enhancing the interactions between endothelial cells and smooth muscle cells (Suri, et al., Cell 87:1171-80. (1996), Papapetropoulos, et al., Lab Invest 79:213-23. (1999)). Over-expression of Ang-2 in mice causes embryonic lethality with defects in angiogenesis similar to those observed in Ang-1 or Tie2 mutant mice. These findings are consistent with the hypothesis that Ang-2 functions as a natural antagonist of signal transduction pathways mediated by Ang-1.

Although overexpression of either VEGF-A or Ang-1 from the keratinocyte-specific keratin-14 promoter leads to increased angiogenesis in the skin of transgenic mice, the resulting vascular structures are quite different. Expression of VEGF-A alone leads to the formation of numerous small blood vessels that are hyperpermeable (Detmar, et al., J Invest Dermatol 111:1-6. (1998), Thurston, et al., Science 286:2511-4. (1999)). In contrast, expression of Ang-1 primarily results in increased vessel diameter with little increase in vessel number (Thurston, et al., Science 286:2511-4. (1999), Suri, et al., Science 282:468-71. (1998)). Transgenic mice that express both VEGF-A and Ang-1 show increased vascularization of the skin. The increase in vessel density is due to increased vessel number as well as greater vessel diameter. Unlike the vessels formed by VEGF-A overexpression alone, vessels in VEGF/Ang-1 transgenic mice are not hyperpermeable (Thurston, et al., Science 286:2511-4. (1999)). These results are consistent with the proposed role of VEGF-A in promoting the early stages of endothelial cell proliferation and migration and that of Ang-1 in promoting the maturation and stability of nascent vessels. Based on these observations, it is reasonable to speculate that co-expression of VEGF-A and Ang-1 act synergistically to promote the formation of a mature vascular network.

Because of its potent angiogenic effects, VEGF-A gene therapy has been explored as a strategy to increase vascularization of ischemic tissues. Local administration of VEGF121 cDNA in rats led to increased survival of experimentally induced ischemic skin flaps, which was accompanied by an increase in dermal blood vessel density (Taub, et al., Plast Reconstr Surg 102:2033-9. (1998)). In animal models of myocardial microvascular ischemia, administration of VEGF-A led to increased angiogenesis, improved blood flow and reduced ischemia (Tanaka, et al., J Thorac Cardiovasc Surg 120:720-8. (2000)). VEGF-A gene therapy is currently in clinical trials for the treatment of chronic myocardial ischemia (O'Brien and Simari, Mayo Clin Proc 75:831-4. (2000), Baumgartner, Curr Cardiol Rep 2:24-8. (2000), Vale, et al., Circulation 102:965-74. (2000)).

To improve the performance of cultured skin tissue for burns treatment and wound healing, two groups have genetically altered keratinocytes to over-express VEGF. Using human keratinocytes infected with a replication-incompetent retrovirus expressing VEGF165, Supp et al. found that VEGF-A expression accelerated angiogenesis of the cultured skin tissue following engraftment onto mice (Supp, et al., J Invest Dermatol 114:5-13. (2000)). The modified grafts exhibited increased numbers of dermal blood vessels and a decreased time to vascularization. The cultured skin tissue expressing VEGF-A adhered to the wound bed better than controls and bled more upon excision. By three days, blood vessels were observed in the dermal layer of the cultured skin tissue expressing VEGF-A. Immunohistochemical analysis detected mouse endothelial cells in the dermal layers of the grafts. The time to vascularization of the modified grafts was reduced by one week. The cultured skin tissue prepared with VEGF-A keratinocytes continued to express high levels (~140× controls) of VEGF-A after 21 days of in vitro culture. Increased levels of expression were sustained for at least 14 days after grafting.

Del Rio and colleagues have reported the use of non-viral transfection methods to produce pig keratinocytes over-expressing VEGF-A under control of the keratinocyte-specific keratin 5 promoter. These keratinocytes were grown on a composite culture of fibroblast-containing fibrin gels and elicited a strong angiogenic response when grafted onto wounds on nude mice (Del Rio, et al., Gene Therapy 6:1734-1741 (1999)). Elevated VEGF-A expression was detectable 20 days after grafting. These results suggest that enhanced vascularization by VEGF-A may increase the use of cultured skin tissue in impaired healing environments such as chronic skin ulcers or in diabetic wound healing.

The studies described above utilized viral or keratin-5 promoters to direct sustained expression of VEGF-A during graft culture and wound healing. This would not be desirable in a clinical setting, where it would be advantageous to promote angiogenesis only at the beginning of the wound healing process, but not have long-term, sustained overexpression of VEGF at the end of the wound healing process.

Although these studies highlight the utility of VEGF-A for inducing angiogenesis, the results of VEGF overexpression in transgenic mice indicate that expression of VEGF-A alone is insufficient to promote complete angiogenesis. Therefore, development of therapeutic strategies to express VEGF-A along with other angiogenic factors holds great promise to improve the care and healing of chronic wounds.

During wound healing, VEGF-A production transiently increases, leading to increased endothelial cell proliferation and migration into the wound bed. Concomitant with increased VEGF-A expression, increased local expression of Ang-2 antagonizes the vessel-stabilizing influence of Ang-1 and leads to increased plasticity of the vasculature during angiogenesis. As angiogenesis proceeds, VEGF-A and Ang-2 production diminishes and the nascent vasculature is stabilized by continued expression of Ang-1.

To recapitulate the temporal functions of VEGF-A and Ang-1 during engraftment of cultured skin tissue, the present invention contemplates the generation of organotypic skin cultures that transiently express VEGF-A during the process of wound healing and that provide sustained expression of Ang-1 following cessation of VEGF-A expression. To control the timing and extent of VEGF-A and Ang-1 expression during wound healing, the present invention contemplates expression of these proteins in keratinocytes using inducible regulatory systems.

The use of activators of angiogenic genes is also contemplated. In particular, Hypoxia-induced factor (HIF) is a heterodimeric transcription factor composed of the HIF1α subunit and the aryl-hydrocarbon receptor nuclear transporter (ARNT). The HIF1α subunit is constitutively expressed in many tissues, but is rapidly degraded by the ubiquitin/proteasome system under normoxic conditions. This degradation is mediated by a 200 amino acid oxygen destruction domain (ODD) located in the middle of the HIF1α subunit. Under hypoxic conditions, the HIF1α subunit is stabilized, leading to its association with ARNT, translocation to the nucleus, and activation of hypoxia-inducible target genes, including VEGF. Deletion of the ODD results in the production of a HIF1α polypeptide that is stable under normoxic conditions and that induces VEGF and other hypoxia-regulated genes in the absence of a hypoxic stimulus. Accordingly, the present invention provides keratinocytes comprising at least one exogenous gene that encodes an angiogenic factor or activator of an angiogenic factor. In some embodiments, the angiogenic factor is a member of the VEGF family. In further preferred embodiments, the angiogenic factor is VEGF-A (SEQ ID NO:1). The present invention is not limited to the use of wild-type VEGF sequences. Indeed, the use of a variety of VEGF homologs is contemplated. In some preferred embodiments, the VEGF homologs share at least 80% identity with native VEGF sequences, in more preferred embodiments, the VEGF homologs share at least 90% homology with native VEGF sequences, while in most preferred embodiments, the VEGF homologs share at least 95% identity with native VEGF homologs. In other preferred embodiments, the VEGF homologs hybridize to native VEGF sequences under conditions ranging from low to high stringency. In still other embodiments, VEGF proteins encoded by VEGF homologous gene sequences compete with native VEGF in a competitive binding assay (e.g. binding to VEGF receptors flt-1, flt-3, or KDR). In further preferred embodiments, VEGF-A homologs share at least 80% identity with SEQ ID NO:1, in more preferred embodiments, the VEGF-A homologs share at least 90% homology with native SEQ ID NO:1, while in most preferred embodiments, the VEGF-A homologs share at least 95% identity with native SEQ ID NO:1. In other preferred embodiments, the VEGF-A homologs hybridize to SEQ ID NO:1 or its complement under conditions ranging from low to high stringency. In still other embodiments, VEGF proteins encoded by VEGF homologous gene sequences compete with VEGF-A encoded by SEQ ID NO:1 in a competitive binding assay.

In other embodiments, the keratinocytes comprise at least one exogenous gene encoding an angiopoietin. In some embodiments, the angiopoietin shares substantial homology with angiopoietin-1 (ANG-1). In further preferred embodiments, the angiogenic factor is ANG-1 (SEQ ID NO: 2). The present invention is not limited to the use of wild-type angiopoietin sequences. Indeed, the use of a variety of angiopoietin homologs is contemplated. In some preferred embodiments, the angiopoietin homologs share at least 80% identity with native angiopoietin sequences, in more preferred embodiments, the angiopoietin homologs share at least 90% homology with native angiopoietin sequences, while in most preferred embodiments, the angiopoietin homologs share at least 95% identity with native angiopoietin sequences. In other preferred embodiments, the angiopoietin homologs hybridize to native angiopoietin sequences under conditions ranging from low to high stringency. In still other embodiments, angiopoietin proteins encoded by angiopoietin homologous gene sequences compete with native angiopoietin in a competitive binding assay (e.g., with the TIE2 receptor). In further embodiments, preferred angiopoietin homologs share at least 80% identity with SEQ ID NO:2, in more preferred embodiments, the angiopoietin homologs share at least 90% homology with native SEQ ID NO:2, while in most preferred embodiments, the angiopoietin homologs share at least 95% identity with native SEQ ID NO:2. In other preferred embodiments, the angiopoietin homologs hybridize to SEQ ID NO:2 or its complement under conditions ranging from low to high stringency. In still other embodiments, angiopoietin proteins encoded by angiopoietin homologous gene sequences compete with angiopoietin encoded by SEQ ID NO:2 in a competitive binding assay.

In other embodiments, the keratinocytes comprise at least one exogenous gene encoding an activator of an angiogenesis factor. In some preferred embodiments, the activator is HIF-1α (SEQ ID NO: 3). The present invention is not limited to the use of wild-type HIF-1α sequences. Indeed, the use of a variety of HIF-1α homologs is contemplated. In some preferred embodiments, the HIF-1α homologs share at least 80% identity with native HIF-1α sequences, in more preferred embodiments, the HIF-1α homologs share at least 90% homology with native HIF-1α sequences, while in most preferred embodiments, the HIF-1α homologs share at least 95% identity with native HIF-1α sequences. In other preferred embodiments, the HIF-1α homologs hybridize to native HIF-1α sequences under conditions ranging from low to high stringency. In still other embodiments, HIF-1α proteins encoded by HIF-1α homologous gene sequences compete with native HIF-1α in a competitive binding assay (e.g., with ARNT). In further embodiments, preferred HIF-1α homologs share at least 80% identity with SEQ ID NO:3, in more preferred embodiments, the HIF-1α homologs share at least 90% homology with native SEQ ID NO:3, while in most preferred embodiments, the HIF-1α homologs share at least 95% identity with native SEQ ID NO:3. In other preferred embodiments, the HIF-1α homologs hybridize to SEQ ID NO:3 or its complement under conditions ranging from low to high stringency. In still other embodiments, HIF-1α proteins encoded by HIF-1α homologous gene sequences compete with HIF-1α encoded by SEQ ID NO:3 in a competitive binding assay.

Functional homologs or variants of angiogenic factors and activators described above can be screened for by expressing the variant in an appropriate vector (described in more detail below) in keratinocytes, using the keratinocytes to produce cultured skin tissue, and analyzing the cultured skin tissue for increased vascularization.

In some embodiments, variants (i.e., homologous sequences) result from mutation, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., angiogenic factor function) for such purposes as increasing binding affinity of an angiogenic factor or activator (e.g., VEGF-A, ANG-1, or HIF-1α) for its ligand. Such modified peptides are considered functional equivalents of peptides having an activity of VEGF-A, ANG-1, or HIF-1α as defined herein. A modified peptide can be produced in which the nucleotide sequence encoding the polypeptide has been altered, such as by substitution, deletion, or addition. In particularly preferred embodiments, these modifications do not significantly reduce the activity of the modified VEGF-A, ANG-1, or HIF-1α. In other words, construct "X" can be evaluated in order to determine whether it is a member of the genus of modified or variant angiogenic factors of the present invention as defined functionally, rather than structurally. In preferred embodiments, the activity of variant or mutant VEGF-A, ANG-1, or HIF-1α is evaluated by the methods described above.

Moreover, as described above, variant forms of VEGF-A, ANG-1, and HIF-1α are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of VEGF-A, ANG-1, and HIF-1 disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

In some preferred embodiments, the keratinocytes of the present invention comprise at least one copy of a VEGF homolog and/or at least one copy of an angiopoietin homolog, and/or at least one copy of a HIF-1α homolog. In some preferred embodiments, the keratinocytes of the present invention comprise at least one copy of a VEGF-A homolog (e.g., SEQ ID NO:1) and/or at least one copy of an angiopoietin-1 homolog (e.g., SEQ ID NO:2). NIKS cells expressing VEGF-A have been deposited with the American Type Culture Collection (ATCC), Manassas, Va., as cell line ATCC PTA-9170.

In still further preferred embodiments, at least one angiogenic factor is operably associated with an inducible regulatory system. In some preferred embodiments, the inducible system is the Tet system. This system allows for regulated induction or repression of gene expression controlled by the presence or absence of tetracycline or tetracycline derivatives, including, but not limited to doxycycline (Gossen and Bujard, Proc Natl Acad Sci USA 89:5547-51 (1992), Gossen, et al., Curr Opin Biotechnol 5:516-20. (1994), Gossen, et al., Science 268:1766-9 (1995)). Other suitable inducible expression systems include GENESWITCH. Accordingly, the present invention provides constructs for transfecting keratinocytes or other cells comprising an inducible promoter system in operable association with an angiogenic factor or activator gene (e.g., VEGF, ANG-1, or HIF-1α). In still further embodiments, the exogenous genes are operably attached to a promotor that is inducible by the topical application of an inducing factor (e.g., topical application of doxycycline to induce the Tet-on promoter; see FIG. 4).

In some further preferred embodiments, the angiogenic factors and/or activators are operably linked to different inducible promoters so that the genes can be expressed at different times. For example, in some embodiments, it is contemplated that the VEGF gene is expressed first in the graft tissue, followed by the expression of the ANG-1 gene. In still other embodiments, it is contemplated that the keratinocytes (e.g., NIKS cells) are transfected with only one of the angiogenic factors or activators. It is contemplated that populations of keratinocytes expressing the different angigenic factors or activators can be mixed in different ratios, thereby modulating the expression levels of the gene products in the resulting graft tissues. For example, in some embodiments, 90% of the keratinocytes used to form a graft express VEGF-A, while 10% of the keratinocytes express ANG-1. In other embodiments, 70% of the keratinocytes used to form a graft express VEGF-A, while 30% of the keratinocytes express ANG-1. In other embodiments, 30% of the keratinocytes used to form a graft express VEGF-A, while 70% of the keratinocytes express ANG-1. In other embodiments, 10% of the keratinocytes used to form a graft express VEGF-A, while 90% of the keratinocytes express ANG-1. It will be recognized that these ranges are not limiting and are intended to provide guidance for determining the optimal ratios of angiogenic factor or activator expressing cells.

The constructs of the present invention may be introduced into keratinocytes by a variety of methods. In particularly preferred embodiments, the constructs are introduced via the TRANSIT system (Mirus Corp., Madison, Wis.). In general, it is contemplated that a number of other mammalian expression vectors are suitable for use in the present invention, including, but not limited to, pWLNEO, pSV2CAT, pOG44, pXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements. Additionally, the exogenous gene may be inserted via a retroviral vector. In particularly preferred embodiments, the retroviral vector is pseudotyped retroviral vector (Clontech, Palo Alto, Calif.). It is contemplated that transfection can be accomplished by any method known in the art, including but not limited to calcium-phosphate coprecipitation, electroporation, microparticle bombardment, liposome mediated transfection, or retroviral infection.

In some embodiments, the keratinocytes are utilized to form cultured skin tissue. In preferred embodiments, the keratinocytes are organotypically cultured. In particularly preferred embodiments, a dermal layer comprising collagen and fibroblasts is formed and cultured. The transfected keratinocytes are then seeded on the dermal equivalent. The seeded dermal equivalent is then cultured at the air interface, eventually forming fully stratified cultured skin tissue. Preferred methods for organotypic culture of skin tissue are described in the examples. However, the present invention is not limited to these preferred culture methods.

C. Uses of Cultured Skin Tissue

It is contemplated that the cultured skin tissue of the present invention has a variety of uses. These uses include, but are not limited to, use for screening compounds, substrates for culturing tumors and pathological agents (e.g., human papilloma virus) for wound closure and burn treatment, and for delivering therapeutic reagents. These uses are described in more detail below.

1. Use for Screening Compounds

The cultured skin tissue of the present invention may be used for a variety of in vitro tests. In particular, cultured skin tissue finds use in the evaluation of: skin care products, drug metabolism, cellular responses to test compounds, wound healing, phototoxicity, dermal irritation, dermal inflammation, skin corrosivity, and cell damage. The cultured skin tissue is provided in a variety of formats for testing, including 6-well, 24-well, and 96-well plates. Additionally, the cultured skin tissue can be divided by standard dissection techniques and then tested. The cultured skin tissue of the present invention may have both an epidermal layer with a differentiated stratum corneum and dermal layer that includes dermal fibroblasts. As described above, in preferred embodiments, the epidermal layer is derived from immortalized NIKS cells. Other preferred cell lines, including NIKS cells are characterized by; i) being immortalized; ii) being nontumorigenic; iii) forming cornified envelopes when induced to differentiate; iv) undergoing normal squamous differentiation in organotypic culture; and v) maintaining cell type-specific growth requirements, wherein said cell type-specific growth requirements include 1) exhibition of morphological characteristics of normal human keratinocytes when cultured in standard keratinocyte growth medium in the presence of mitomycin C-treated 3T3 feeder cells; 2) dependence on epidermal growth factor for growth; and 3) inhibition of growth by transforming growth factor $\beta1$.

The present invention encompasses a variety of screening assays. In some embodiments, the screening method comprises providing cultured skin tissue of the present invention and at least one test compound or product (e.g., a skin care product such as a moisturizer, cosmetic, dye, or fragrance; the products can be in any from, including, but not limited to, creams, lotions, liquids and sprays), applying the product or test compound to the cultured skin tissue, and assaying the effect of the product or test compound on the cultured skin tissue. A wide variety of assays are used to determine the effect of the product or test compound on the cultured skin tissue. These assays include, but are not limited to, MTT cytotoxicity assays (Gay, The Living Skin Equivalent as an In Vitro Model for Ranking the Toxic Potential of Dermal Irritants, Toxic. In Vitro (1992)) and ELISA to assay the release of inflammatory modulators (e.g., prostaglandin E2, prostacyclin, and interleukin-1-alpha) and chemoattractants. The assays can be further directed to the toxicity, potency, or efficacy of the compound or product. Additionally, the effect of the compound or product on growth, barrier function, or tissue strength can be tested.

In particular, the present invention contemplates the use of cultured skin tissue for high throughput screening of compounds from combinatorial libraries (e.g., libraries containing greater than $10^4$ compounds). In some embodiments, the cells are used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, cultured skin tissue is treated with a compound or plurality of compounds (e.g., from a combinatorial library) and assayed for the presence or absence of a second messenger response. In some preferred embodiments, the cells (e.g., NIKS cells) used to create cultured skin tissue are transfected with an expression vector encoding a recombinant cell surface receptor, ion-channel, voltage gated channel or some other protein of interest involved in a signaling cascade. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, IP3, cAMP, arachidonic acid release) due to stimulation of membrane receptors and ion channels (e.g., ligand gated ion channels; see Denyer et al., Drug Discov. Today 3:323-32 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the cells comprising cultured skin tissue are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75-80 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cultured skin tissue of the present invention is also useful in reporter gene assays. Reporter gene assays involve the use of host cells transfected with vectors encoding a nucleic acid comprising transcriptional control elements of a target gene (i.e., a gene that controls the biological expression and function of a disease target or inflammatory response) spliced to a coding sequence for a reporter gene. Therefore, activation of the target gene results in activation of the reporter gene product. This serves as indicator of response such an inflammatory response. Therefore, in some embodiments, the reporter gene construct comprises the 5' regulatory region (e.g., promoters and/or enhancers) of a protein that is induced due to skin inflammation or irritation or protein that is involved in the synthesis of compounds produced in response to inflammation or irritation (e.g., prostaglandin or prostacyclin) operably linked to a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

In other preferred embodiments, cultured skin tissue finds use for screening the efficacy of drug introduction across the skin or the affect of drugs directed to the skin. In these embodiments, cultured skin tissue is treated with the drug delivery system or drug, and the permeation, penetration, or retention or the drug into the skin equivalent is assayed. Methods for assaying drug permeation are provided in Asbill et al., Pharm Res. 17(9): 1092-97 (2000). In some embodiments, cultured skin tissue is mounted on top of modified Franz diffusion cells. The cultured skin tissue is allowed to hydrate for one hour and then pretreated for one hour with propylene glycol. A saturated suspension of the model drug in propylene glycol is then added to the cultured skin tissue. The cultured skin tissue can then be sampled at predetermined intervals. The cultured skin tissue is then analyzed by HPLC to determine the concentration of the drug in the sample. Log P values for the drugs can be determined using the ACD program (Advanced Chemistry Inc., Ontario, Canada). These methods may be adapted to study the delivery of drugs via transdermal patches or other delivery modes.

2. Substrates for Culturing Tumors and Pathological Agents

It is contemplated that cultured skin tissue of the present invention is also useful for the culture and study of tumors that occur naturally in the skin as well as for the culture and study of pathogens that affect the skin. Accordingly, in some embodiments, it contemplated that the cultured skin tissue of the present invention is seeded with malignant cells. By way of non-limiting example, the cultured skin tissue can be seeded with malignant SCC13y cells as described in U.S. Pat. No. 5,989,837, which is incorporated herein by reference, to provide a model of human squamous cell carcinoma. These seeded cultured skin tissue can then be used to screen compounds or other treatment strategies (e.g., radiation or tomotherapy) for efficacy against the tumor in its natural environment. Thus, some embodiments of the present invention provide methods comprising providing cultured skin tissue comprising malignant cells or a tumor and at least one test compound, treating the cultured skin tissue with the compound, and assaying the effect of the treatment on the malignant cells or tumors. In other embodiments of the present invention, methods are provided that comprise providing cultured skin tissue comprising malignant cells or a tumor and at least one test therapy (e.g., radiation or phototherapy, treating the cultured skin tissue with the therapy, and assaying the effect of the therapy on the malignant cells or tumors.

In other embodiments, cultured skin tissue is used to culture and study skin pathogens. By way of non-limiting example, cultured skin tissue is infected with human papilloma virus (HPV) such as HPV18. Methods for preparing cultured skin tissue infected with HPV are described in U.S. Pat. No. 5,994,115, which is incorporated herein by reference. Thus, some embodiments of the present invention provide methods comprising providing cultured skin tissue infected with a pathogen of interest and at least one test compound or treatment and treating the cultured skin tissue with the test compound or treatment. In some preferred embodiments, the methods further comprise assaying the effect the test compound or treatment on the pathogen. Such assays may be conducted by assaying the presence, absence, or quantity of the pathogen in the cultured skin tissue following treatment. For example, an ELISA may be performed to detect or quantify the pathogen. In some particularly preferred embodiments, the pathogen is viral pathogen such as HPV.

3. Wound Closure and Burn Treatment

The cultured skin tissue of the present invention finds use in wound closure and burn treatment applications. The use of auto grafts and allografts for the treatment of burns and wound closure is described in Myers et al., A. J. Surg. 170 (1):75-83 (1995) and U.S. Pat. Nos. 5,693,332; 5,658,331; and 6,039,760, each of which is incorporated herein by reference. In some embodiments, the cultured skin tissue may be used in conjunction with dermal replacements such as DERMAGRAFT. In other embodiments, the cultured skin tissue is produced using both a standard source of keratinocytes (e.g., NIKS cells) and keratinocytes from the patient that will receive the graft. Therefore, the cultured skin tissue contains keratinocytes from two different sources. Accordingly, the present invention provides methods for wound closure, including wounds caused by burns, comprising providing cultured skin tissue having improved vascularization properties according to the present invention and a patient suffering from a wound and treating the patient with the cultured skin tissue under conditions such that the wound is closed.

In still further embodiments, the cultured skin tissue is engineered to provide a therapeutic agent to a subject. In some embodiments, the keratinocytes used to form the cultured skin tissue are transfected with a DNA construct encoding a therapeutic protein (e.g., insulin, clotting factor IX, erythropoietin, etc) and the cultured skin tissue is grafted onto the subject. The therapeutic agent is then delivered to the patient's bloodstream from the graft.

4. Delivery of Therapeutic Reagents

In still further embodiments, the skin tissue is engineered to provide a therapeutic agent to a subject. The present invention is not limited to the delivery of any particular therapeutic agent. Indeed, it is contemplated that a variety of therapeutic agents may be delivered to the subject, including, but not limited to, enzymes, peptides, peptide hormones, other proteins, ribosomal RNA, ribozymes, and antisense RNA. These therapeutic agents may be delivered for a variety of purposes, including but not limited to the purpose of correcting genetic defects. In some particular preferred embodiments, the therapeutic agent is delivered for the purpose of detoxifying a patient with an inherited inborn error of metabolism (e.g., aminoacidopathies) in which the graft serves as wild-type tissue. It is contemplated that delivery of the therapeutic agent corrects the defect. In some embodiments, the keratinocytes used to form the skin equivalent are transfected with a DNA construct encoding a therapeutic agent (e.g., insulin, clotting factor IX, erythropoietin, etc) and the skin equivalent is grafted onto the subject. The therapeutic agent is then delivered to the patient's bloodstream or other tissues from the graft. In preferred embodiments, the nucleic acid encoding the therapeutic agent is operably linked to a suitable promoter. The present invention is not limited to the use of any particular promoter. Indeed, the use of a variety of promoters is contemplated, including, but not limited to, inducible, constitutive, tissue specific, and keratinocyte specific promoters. In some embodiments, the nucleic acid encoding the therapeutic agent is introduced directly into the keratinocytes (i.e., by calcium phosphate co-precipitation or via liposome transfection). In other preferred embodiments, the nucleic acid encoding the therapeutic agent is provided as a vector and the vector is introduced into the keratinocytes by methods known in the art. In some embodiments, the vector is an episomal vector such as a plasmid. In other embodiments, the vector integrates into the genome of the keratinocytes. Examples of integrating vectors include, but are not limited to, retroviral vectors, adeno-associated virus vectors, and transposon vectors.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); ml (milliliters); $\mu$l (microliters); cm (centimeters); mm (millimeters); $\mu$m (micrometers); nm (nanometers); C (degrees Centigrade); U (units), mU (milliunits); min. (minutes); sec. (seconds); % (percent); kb (kilobase); bp (base pair); PCR (polymerase chain reaction); BSA (bovine serum albumin).

Example 1

This example describes culture methods common to the following examples unless otherwise noted.

Media. The organotypic culture process uses six different culture media: 3T3 feeder cell medium (TM); fibroblast growth medium (FM); NIKS medium (NM); plating medium (PM); stratification medium A (SMA); and stratification medium B (SMB). TM is used to propagate 3T3 cells that act as feeder cells for NIKS cells in monolayer culture. TM is a mixture of Dulbecco's modified Eagle's medium (DME, GibcoBRL) supplemented with 10% calf serum (Hyclone). FM is a mixture of Ham's F-12 medium (GibcoBRL) and 10% Fetal Clone II (Hyclone) serum. NM is used to grow NIKS keratinocytes. NM is a 3:1 mixture of Ham's F-12 medium (GibcoBRL) and DME supplemented with 2.5% Fetal Clone II (Hyclone), 0.4 $\mu$g/ml hydrocortisone (Calbiochem), 8.4 ng/ml cholera toxin (ICN), 5 $\mu$g/ml insulin (GibcoBRL), 24 $\mu$g/ml adenine (Sigma) and 10 ng/ml epidermal growth factor (EGF, R&D systems). PM is the medium used when NIKS cells are seeded onto a dermal equivalent. PM is the same as NM except that EGF is removed, $CaCl_2$ (Sigma) is supplemented to a final calcium concentration of 1.88 mM, and only 0.2% Fetal Clone II serum is added. SMA is the same as PM with the addition of 1 mg/ml bovine serum albumin (BSA), 1 $\mu$M isoproterenol, 10 $\mu$M carnitine, 10 $\mu$M serine, 25 $\mu$M oleic acid, 15 $\mu$M linoleic acid, 7 $\mu$M arachidonic acid, 1 $\mu$M $\alpha$-tocopherol, 0.05 mg/ml ascorbic acid (all from Sigma), and 1 ng/ml EGF. SMB is used during the epidermal stratification phase of small format skin equivalent and graft format skin equivalent growth. SMB is the same as SMA but without the presence of the Fetal Clone II serum supplement.

Feeder preparation. Prior to starting test format skin equivalent or graft format skin equivalent organotypic cultures, 3T3 feeder cells are prepared and then used either fresh or frozen for later use. 3T3 cells are grown to confluence and treated with mitomycin-C (4 ug/ml of mitomycin-C in TM, Roche) for two hours. The cells are then washed, resuspended, and plated at a density of $1.25 \times 10^6$ per 100 mm tissue culture dish to support NIKS growth. If frozen feeders are used, a single frozen ampoule containing 1 ml with $2.5 \times 10^6$ is thawed, diluted with fresh TM and plated onto one or more 100 mm tissue culture dishes. This is done for as many dishes as will be needed for NIKS cell growth one day prior to plating the NIKS cells.

Dermal equivalent preparation. Frozen NHDF cells are thawed and plated. The cells are fed FM the next day to remove residual cryoprotectant and subsequently to maintain cell growth. Preconfluent NHDF cells are harvested for use in the dermal equivalent. To prepare the dermal equivalent, rat tail tendon collagen (Type I, Becton-Dickinson) is first diluted to 3 mg/ml in 0.03N acetic acid and chilled on ice. A mixture of concentrated Ham's F12 medium (8.7x normal strength, buffered with HEPES at pH 7.5) is mixed with Fetal Clone II. These two solutions are 11.5 and 10% of the final solution volume. 1 N NaOH is added to the medium mixture (2.5% of final solution). The diluted collagen (74%) is then added to the mixture. A 2% volume of suspended fibroblasts ($2.5 \times 10^6$ cells/ml for the dermal equivalent of test format skin equivalents and $1 \times 10^6$ for dermal equivalent of graft format skin equivalents) is added to the mixture. The solution is mixed gently but thoroughly. 100 $\mu$l is aliquoted into tissue culture inserts (MILLICELL from Millipore Corp.) placed 25 in a 100 mm tissue culture dish for test format skin equivalents. The graft format skin equivalent uses TRANSWELL inserts from Corning. A 13 ml dermal equivalent is poured into each insert making it roughly three times the thickness of a test format dermal equivalent. After 30 minutes for gel formation, the dish containing test format dermal equivalents is flooded with 20 ml of FM. One or two drops FM are placed on the surface of each test format dermal equivalent. For graft format dermal equivalents, 80 ml of FM is placed around the TRANSWELL insert in a 150 mm tissue culture dish and 10 ml is placed on top of the dermal equivalent. The inserts are placed in 37° C., 5% $CO_2$, 90% relative humidity incubator until used. One day prior to seeding the dermal equivalents with NIKS cells, they are lifted to the air interface by placing them onto a sterile stainless steel mesh with two wicking pads (S&S Biopath) on top to supply medium through the bottom of the tissue culture insert.

NIKS Growth and Seeding. Feeders are prepared fresh or thawed and plated in TM one day prior to NIKS plating. NIKS cells are plated onto the feeders at a density of approximately $3 \times 10^5$ cells per 100 mm dish. If the NIKS cells are newly thawed, they are fed fresh NM one day post-plating to remove residual cryoprotectant. The NIKS cells are fed NM to maintain growth as required. When cells approach confluence, the NIKS cells are harvested, counted, and resuspended in PM. $4.65 \times 10^5$ NIKS cells/$cm^2$ are seeded onto the surface of the MIILLICELL or TRANSWELL dermal equivalents, which have been lifted to the air interface for one day. The dishes are fed PM to flood underneath the metal lifter and placed back into the incubator. Two days later, the cultures are fed SMA. After an additional two days, the cultures are fed SMB and

Example 2

Expression Vector Constructs

A cDNA encoding VEGF165 was isolated by PCR using primers based on published sequences (Houck, et al., Mol Endocrinol 5:1806-14. (1991)). The coding region for VEGF165 was cloned into the pTRE2 expression vector (Clontech, Palo Alto, Calif.). This vector contains a minimal CMV promoter flanked by seven repeats of the Tet operator. The integrity of the cloned VEGF-A PCR product was confirmed by restriction analysis and DNA sequencing using VEGF-specific primers.

The coding region for Ang-1 was isolated by PCR from total RNA using primers derived from the published Ang-1 sequence (Maisonpierre, et al., Science 277:55-60. (1997)). The coding region for Ang-1 was cloned into the pTRE2 expression vector and the integrity of the Ang-1 coding region was verified by restriction analysis and DNA sequencing using primers derived from the known Ang-1 sequence.

The coding regions for VEGF165 and Ang-1 also were cloned into an expression vector containing a 2.3 kb fragment of the keratin 14 (K14) promoter. This vector also has a 1.2 kb DNA fragment containing an intron and polyadenlyation signal from the rabbit beta-globin gene. The vectors also contain an expression cassette that confers resistance to the antibiotic blasticidin so that cells that have stably incorporated the expression constructs into their genomes may be selected. The structures of the final expression constructs were confirmed by restriction analysis and DNA sequencing.

The coding region for VEGF165 also was cloned into an expression vector containing a 1.2 kb fragment of the human ubiquitin C (Ub) promoter. This vector also has a 1.2 kb DNA fragment containing an intron and polyadenlyation signal from the rabbit beta-globin gene. The vector also contains an expression cassette that confers resistance to the antibiotic blasticidin so that cells that have stably incorporated the expression construct into their genomes may be selected. The structure of the final expression construct was confirmed by restriction analysis and DNA sequencing.

The coding region for HIF1α was isolated by PCR using primers derived from the published HIF1α sequence. The coding region for HIF1α was cloned into the PCR2.1 vector and the integrity of the HIF1α coding region was verified by restriction analysis and DNA sequencing using primers derived from the known HIF1α sequence.

Example 3

Inducible Expression of VEGF

Purified DNA from the pTRE2/VEGF165 vector was introduced into NIKS cells along with the pTet-On plasmid (Clontech, Palo Alto, Calif.), which encodes a derivative of the tet repressor protein. This protein, rtTA, binds to the tet operator in the presence of doxycycline and will induce expression of VEGF165 when doxycycline is present in the culture medium (see FIG. 4).

NIKS cells were transfected using TransIt-Keratinocyte reagent (Mirus Corporation). Initially, unselected populations of transfected cells were analyzed for VEGF165 expression to confirm that VEGF-A expression was induced by the presence of doxycycline. Twenty-four hours after transfection, cells were incubated with media containing doxycycline (0, 1, 10, 100, 1000 ng/ml) to induce VEGF-A expression and secretion. Media was collected 24 hr after doxycycline addition and the level of VEGF165 was determined by Western blotting using commercially-available antibodies (R&D Systems).

Medium from NIKS cells transfected with the pTet-ON vector alone contained 600 pg/ml VEGF. Medium from cells co-transfected with pTet-ON and pTRE-VEGF in the absence of doxycycline contained 1500 pg/ml VEGF, reflecting a low level of expression from the TRE-VEGF construct in the absence of induction. Following addition of 10 ng/ml or 1000 ng/ml doxycycline, the level of VEGF in the media increased to approximately 6000 pg/ml. Thus, in transiently-transfected cells, the level of induced VEGF was 10-fold higher than in control cells.

Example 4

Repressible Expression of Ang-1

Purified DNA from the pTRE2/Ang-1 vector was introduced into NIKS cells along with the pTet-Off plasmid (Clontech, Palo Alto, Calif.), which encodes a derivative of the tet repressor protein. This protein, tTA, binds to the tet operator in the absence of doxycycline and will induce expression of Ang-1 when doxycycline is not present in the culture medium. Unselected populations of transfected cells were analyzed for Ang-1 expression to confirm that Ang-1 expression was repressed by the presence of doxycycline. Twenty-four hours after transfection, cells are incubated with media containing doxycycline (0, 1, 10, 100, 1000 ng/ml) to inhibit Ang-1 expression and secretion.

Media was collected 24 hr after doxycycline addition and the level of Ang-1 was determined by Western blotting using a commercially available antibody (Santa Cruz Biotechnology). Multiple Ang-1 bands, representing variable glycosylation patterns, were detected by Western blot in media samples from cells transfected with the pTRE2/Ang-1 and pTet-OFF plasmids. No Ang-1 bands were seen in media from cells transfected with the pTet-OFF plasmid alone.

Total RNA isolated from transfected cells was analyzed by RT-PCR using primers that amplified Ang-1 RNA expressed from the pTRE2/Ang-1 vector, but not from the endogenous Ang-1 gene. A strong Ang-1 RT-PCR product was observed in RNA from cells transfected with the pTRE2/Ang-1 and pTet-OFF plasmids. The intensity of this product was reduced following addition of doxycycline, demonstrating that expression of Ang-1 from this vector was repressed by doxycycline.

Example 5

Expression of VEGF from the K14 Promoter

Purified DNA from the pK14-VEGF165 vector was introduced into NIKS cells using TransIt-Keratinocyte reagent (Mirus Corporation). Twenty-four hours after transfection, medium was collected and the level of VEGF protein was determined by ELISA. Media from transiently-transfected NIKS cells contained 12-fold more VEGF (10.75 ng/ml) than media from control cells (0.89 ng/ml).

Total RNA was also isolated from transfected cells and expression of VEGF165 mRNA from the K14-VEGF construct was monitored by RT-PCR. Transgene-specific expression was detected using primers that amplify VEGF165 mRNA expressed from the K14-VEGF construct but that do not amplify VEGF RNA from the endogenous VEGF gene. A VEGF165 RT-PCR product was detected in RNA from transfected cells, but was not detected in RNA from control cells. RT-PCR reactions were also performed with primers that amplified all three VEGF splice variants from the endogenous gene as well as the VEGF165 mRNA expressed from the K14-VEGF expression construct.

Example 6

Expression of VEGF from the Ubiquitin Promoter

Purified DNA from the pUb-VEGF165 vector was introduced into NIKS cells using TransIt-Keratinocyte reagent (Mirus Corporation). Twenty-four hours after transfection, medium was collected and the level of VEGF protein was determined by ELISA. Media from transiently-transfected NIKS cells contained 10-fold more VEGF (9.38 ng/ml) than media from control cells (0.89 ng/ml).

Total RNA was also isolated from transfected cells and expression of VEGF165 mRNA from the pUb-VEGF construct was monitored by RT-PCR. Transgene-specific expression was detected using primers that amplify VEGF165 mRNA expressed from the pUb-VEGF construct but that do not amplify VEGF RNA from the endogenous VEGF gene. A VEGF165 RT-PCR product was detected in RNA from transfected cells, but was not detected in RNA from control cells. RT-PCR reactions were also performed with primers that amplified all three VEGF splice variants from the endogenous gene as well as the VEGF165 mRNA expressed from the pUb-VEGF expression construct.

Example 7

Expression of Ang-1 from the K14 Promoter

Purified DNA from the pK14-Ang1 vector was introduced into NIKS cells using TransIt-Keratinocyte reagent (Mirus Corporation). Twenty-four hours after transfection, medium was collected and the level of Ang-1 protein was determined by Western blot. Multiple Ang-1 bands, presumably resulting from variable glycosylation of Ang-1, were seen in media from cells transfected with the K14-Ang1 expression construct. No Ang-1 bands were observed in media from cells transfected with the empty K14 vector.

Total RNA was also isolated from transfected cells and expression of Ang-1 mRNA from the K14-Ang1 construct was monitored by RT-PCR. Transgene-specific expression was detected using primers that amplify Ang-1 mRNA expressed from the K14-Ang1 construct but that do not amplify Ang-1 RNA from the endogenous Ang-1 gene. An Ang-1 RT-PCR product was detected in RNA from transfected cells, but was not detected in RNA from control cells.

Example 8

Selection and Characterization of Stable Transfectants

Both VEGF-A and Ang-1 are secreted proteins and therefore need not be expressed in all cells of a tissue to promote angiogenesis. In order to independently control expression of VEGF-A and Ang-1, separate cell lines were generated that express VEGF-A or Ang-1. These cells can be mixed subsequently to form co-cultures that contain both VEGF- and Ang-1 expressing cells.

Blasticidin has been used to select for stably transfected keratinocytes that can regenerate normal epidermal architecture (Deng, et al., Biotechniques 25:274-80. (1998)). The pUb-VEGF165 and pK14-VEGF165 expression constructs contain a gene encoding a protein that confers resistance to blasticidin to allow for selection of stably-transfected cells. NIKS cells were transfected with the pK14-VEGF165 and pUb-VEGF165 plasmids. Transfected cells are selected by growth in media containing blasticidin (2.5 µg/ml), which killed any NIKS cells that had not incorporated the plasmids into their genome. Clonal populations of stably transfected NIKS cells were isolated by seeding blasticidin-selected transfected cells at low density on a feeder layer of blasticidin-resistant 3T3 cells. Cell lines that express Ang-1 were generated by transfection of NIKS cells with the pK14-Ang1 plasmid, followed by selection of stably-transfected cells using blasticidin.

Stable cell lines that contain the pK14-VEGF165, pUb-VEGF165, and pK14-Ang1 plasmids were identified by examining multiple clonal cell lines by RT-PCR. Individual clonal cell lines that possess intact copies of the pK14-VEGF165, pUb-VEGF165, and pK14-Ang1 transgenes were expanded in the presence of blasticidin and frozen in culture media containing 10% glycerol to generate permanent stocks of each line.

The level of transgene expression in each clone was monitored by RT-PCR using primers that amplified mRNA expressed from the transgenes, but not the endogenous genes. Clones that showed strong transgene expression were also examined by RT-PCR using primers that amplified both the transgene-expressed and endogenous mRNA species. Clones were identified with both the pK14-VEGF165 and pUb-VEGF165 constructs that specifically overexpressed the VEGF165 isoform relative to the VEGF121 and VEGF189 isoforms.

Example 9

Analysis of VEGF Expression in Organotypic Culture

Clones of NIKS cells stably-transfected with the pK14-VEGF165 expression construct and untransfected NIKS cells were grown in organotypic culture to produce cultured skin tissue. Total RNA was isolated from the cultured skin tissue and expression of the VEGF165 transgene was analyzed by RT-PCR. A transgene-specific RT-PCR product was amplified from skin tissue containing the K14-VEGF165 construct, but was not detected in skin tissue prepared from untransfected NIKS cells.

The level of VEGF in media samples from skin tissue prepared from control cells and from NIKS cells stably-transfected with the pK14-VEGF165 expression construct was determined by ELISA. Comparable levels of VEGF protein were detected in control and K14-VEGF transgenic skin tissue.

Example 10

Cell Proliferation Assays

VEGF-A is a potent and specific mitogen for microvascular endothelial cells (HMVECs) (Detmar, et al., J Invest Dermatol 105:44-50. (1995)). Conditioned medium from cells expressing VEGF-A promotes proliferation of microvascular endothelial cells (Ferrara and Henzel, Biochem Biophys Res Commun 161:851-8. (1989), Supp, et al., J Invest Dermatol 114:5-13. (2000)). Control or conditioned media from cultures expressing VEGF-A was added at different concentrations to triplicate cultures of HMVECs (Cascade Biologics, Portland, Oreg.). Cells were fed with fresh conditioned medium after 48 hours and incubated for an additional 48 hours to allow cell proliferation. Mitogenic effects of VEGF-A were determined by counting trypsinized cultures in a hemocytometer. Cultures fed with media collected from cells transfected with the pK14-VEGF165 expression construct contained twice as many cells ($4\times10^4$) as cultures fed with media collected from cells transfected with the empty K14 vector ($2\times10^4$).

Example 11

Inducible Expression of HIF-1α

The HIF1α coding region is cloned into the pTRE2 expression vector (Clontech, Palo Alto, Calif.). This vector contains a minimal CMV promoter flanked by seven repeats of the Tet operator. The integrity of the cloned HIF1α PCR product is confirmed by restriction analysis and DNA sequencing using HIF1α-specific primers.

Purified DNA from the pTRE2/HIF1α vector is introduced into NIKS cells along with the pTet-On plasmid (Clontech, Palo Alto, Calif.), which encodes a derivative of the tet repressor protein. This protein, rtTA, binds to the tet operator in the presence of doxycycline and will induce expression of HIF1α when doxycycline is present in the culture medium.

NIKS cells are transfected using TransIt-Keratinocyte reagent (Mirus Corporation). Initially, unselected populations of transfected cells are analyzed for HIF1α expression to confirm that HIF1α expression is induced by the presence of doxycycline. Twenty-four hours after transfection, cells are incubated with media containing doxycycline (0, 1, 10, 100, 1000 ng/ml) to induce HIF1α expression.

Example 12

Analysis of Inducible VEGF165 and Ang-1 Expression

Clones of NIKS that express inducible, increased levels of VEGF165 are identified by screening culture media from blasticidin-resistant colonies for the presence of VEGF165. Multiple clones that contain intact copies of the pTet-On(bsd) and pTRE2/VEGF-A plasmids are examined for expression of VEGF-A in the presence of doxycycline. Cells are incubated with media containing doxycycline (0, 1, 10, 100, 1000 ng/ml) to induce VEGF-A expression and secretion. Media is collected at 24 hr after doxycycline addition and the level of VEGF165 is determined by Western blotting using commercially available antibodies (R&D Systems).

Multiple clonal cell lines containing intact copies of the pTRE2/Ang-1 and pTet-Off(bsd) plasmids are examined for Ang-1 expression. Cells are incubated with media containing doxycycline (0, 1, 10, 100, 1000 ng/ml) to inhibit Ang-1 expression. Media is collected at 24 hr after doxycycline addition and the level of Ang-1 is determined by Western blot using anti-Ang-1 antibodies (Research Diagnostics, Inc., Flanders N.J.).

Multiple clonal cell lines containing intact copies of the pTRE2/HIF1α and pTet-On(bsd) plasmids are examined for HIF1α expression. Cells are incubated with media containing doxycycline (0, 1, 10, 100, 1000 ng/ml) to induce HIF1α expression. Cells are harvested 24 hr after doxycycline addition and the level of HIF1α mRNA is determined by RT-PCR.

Example 13

Inducible VEGF165 and Ang-1 Expression in Organotypic NIKS Cultures

NIKS cell clones that exhibit doxycycline-inducible VEGF165 expression and doxycycline-repressible Ang-1 expression are used to prepare organotypic skin cultures using the methods and conditions of Example 1. Histological sections of organotypic cultures formed by genetically modified NIKS cells are compared to cultures prepared from unmodified NIKS cells. Tissue sections are stained with hematoxylin and eosin to visualize the stratified epidermal layers.

The organotypic cultures in the initial expression studies are prepared using cells individually expressing VEGF-A or Ang-1. Subsequently, organotypic cultures are prepared by seeding dermal equivalents with a mixture of VEGF-A and Ang-1 expressing cells. In these mixed cultures, Ang-1 is expressed when doxycycline is absent from the medium, but VEGF-A is not expressed. When doxycycline is added to the medium, the expression of Ang-1 is repressed, while the expression of VEGF-A is induced. In this way, differential expression of Ang-1 and VEGF can be achieved by incubation with a single inducing agent. Different ratios of VEGF-A and Ang-1 expression levels can be achieved by varying the ratio of VEGF-A and Ang-1 expressing cells used to prepare subsequent organotypic cultures. In addition, organotypic cultures can be prepared with mixtures of Ang-1 and VEGF-A expressing NIKS cells along with unmodified NIKS cells to provide further flexibility in protein expression in the cultures.

To monitor changes in VEGF165 and Ang-1 expression levels in organotypic cultures, media underlying the cultures is harvested at various times prior to and following doxycycline addition. When organotypic cultures are 10 days old, doxycycline (0, 1, 10, 100, 1000 ng/ml) is added to the culture medium. Cultures are incubated for 48 hours in the presence of doxycycline to allow for induction of VEGF-A and repression of Ang-1. After 48 hours in the presence of doxycycline, cultures are fed with media lacking doxycycline. Media is harvested every 12 hours for four days after doxycycline addition and the levels of VEGF-A and Ang-1 proteins in the media is determined by ELISA.

Example 14

Alternative Inducible Expression System

Another heterologous expression system shown to confer inducible protein expression in mammalian cells may be used in the present invention. The GENESWITCH technology (Valentis, Inc. The Woodlands, Tex.) utilizes chimeric transcriptional regulators comprised of the DNA binding domain of GAL4 and a truncated progesterone receptor fused to the VP16 activation domain or KRAB transcriptional repressor domain (Wang, et al., Proc Natl Acad Sci USA 91:8180-4. (1994), Wang, et al., Gene Ther 4:432-41. (1997)). In the presence of mifepristone (RU486), these proteins bind to, and activate or repress transcription from, transgenes flanked by GAL4 binding sites. The VEGF-A, Ang-1, and HIF1α coding regions are cloned into a vector containing 6 GAL4 binding sites and a minimal promoter.

Example 15

Bioassays of VEGF-A and Ang-1

To demonstrate that the VEGF-A and Ang-1 produced by genetically modified NIKS™ organotypic cultures stimulate angiogenesis, in vitro angiogenesis assays are used to characterize VEGF-A and Ang-1. As another indication of VEGF-A mitogenic activity, the percentage of replicating cells in HMVEC cultures exposed to conditioned media is determined by immunostaining with mAb Ki67 (Vector Labs). This antibody specifically reacts with a nucleoprotein complex in actively cycling cells (Gerdes, et al., J Immunol 133:1710-5. (1984), Lopez, et al., Exp Cell Res 210:145-53. (1994)) and is a reliable marker of proliferating cells. Cells are incubated in endothelial cell growth medium containing conditioned medium from NIKS/VEGF-A organotypic cultures for 48 hours. Cells are harvested, washed in PBS, fixed onto microscope slides, and processed for immunocytochemistry using Ki67 as described (Lopez, et al., Exp Cell Res 210:145-53. (1994)). The percentage of proliferative cells is determined for triplicate cultures for each experimental condition.

In Vitro Angiogenesis Assays

Several assays are available to assess the angiogenic properties of VEGF-A and Ang-1. The bioactivity of VEGF-A and Ang-1 secreted by NIKS organotypic cultures is determined using the chick chorioallantoic membrane assay and a fibrin gel endothelial cell-sprouting assay.

Chick Chorioallantoic Membrane Assay

Application of angiogenic growth factors to the chick chorioallantoic membrane (CAM) induces endothelial cell proliferation and formation of new blood vessels (Folkman, Cancer Res 34:2109-13. (1974), Jakob, et al., Exp Pathol (Jena) 15:241-9. (1978), Wilting, et al., Cell Tissue Res 274: 163-72. (1993)). Conditioned medium from NIKS cultures expressing VEGF-A or Ang-1 is concentrated 10-fold by ultrafiltration, applied to Thermanox discs and air-dried. Discs are inverted onto the CAM of day 13 chick embryos and embryos are cultured at 37° C. for 3-5 days. The angiogenic activity of conditioned media is determined by microscopic examination of the CAM for development of brush-like blood vessels compared to CAM exposed to control media. Recombinant VEGF-A (R&D systems, Minneapolis, Minn.) is used as a positive control in CAM angiogenesis assays. Pre-incubation of samples with an antibody that neutralizes VEGF (Mab203, R&D Systems) is performed to demonstrate that angiogenic activity is attributable to VEGF.

In Vitro Endothelial Cell Sprouting Assay

Microvascular endothelial cells cultured on microcarrier beads in a fibrin gel project capillary-like sprouts into the fibrin matrix in response to angiogenic factors, including VEGF-A and Ang-1 (Nehls and Drenckhahn, Microvasc Res 50:311-22. (1995), Koblizek, et al., Curr Biol 8:529-32. (1998)). Airway microvascular endothelial cells (HMVEC-L, Clonetics, Walkersville, Md.) are cultivated to confluence on 175 □m microcarrier beads (Sigma, St Louis, Mo.). Microcarrier beads are suspended in a fibrinogen gel (2.5 mg/ml) containing 200 units/ml aprotinin and 2.5 units/ml thrombin (Sigma, St Louis, Mo.). Conditioned medium from VEGF-A or Ang-1 expressing organotypic cultures is added to the fibrin gels to promote angiogenesis. Cultures are fed daily with media containing conditioned medium or purified recombinant VEGF. After three days of culture, samples are examined by phase contrast microscopy to visualize endothelial sprouts. In vitro angiogenesis is quantified by determining the number and length of sprouts emanating from 10 microcarrier beads grown in the presence or absence of conditioned medium. Experiments are performed in triplicate.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in medicine, cell biology, molecular biology, genetics, or related fields are intended to be within the scope of the following claims.

What is claimed is:

1. A method of treatment of a patient comprising:
   a) providing a human skin equivalent comprising NIKS (Near Diploid Immortalized Keratinocyte) cells, said NIKS cells comprising an exogenous VEGF gene operably linked to a promoter, wherein said NIKS cells are stably transfected with said exogenous VEGF gene, which cells have the characteristics of cells deposited as cell line ATCC PTA-9170; and
   b) contacting said patient with said human skin equivalent.

2. The method of claim 1, wherein said patient is suffering from burns.

3. The method of claim 1, wherein said patient is suffering from a wound.

* * * * *

UNITED STATES PATENT AND TRADEMARK OFFICE
CERTIFICATE OF CORRECTION

| | | |
|---|---|---|
| PATENT NO. | : 7,915,042 B2 | Page 1 of 1 |
| APPLICATION NO. | : 12/392221 | |
| DATED | : March 29, 2011 | |
| INVENTOR(S) | : Allen R. Comer et al. | |

It is certified that error appears in the above-identified patent and that said Letters Patent is hereby corrected as shown below:

In the Specification:

At Column 1, beginning at line 13, please insert the following:

--STATEMENT REGARDING FEDERALLY SPONSORED RESEARCH OR DEVELOPMENT

This invention was made with government support under SBIR grant R43 GM65025-01 awarded by the National Institutes of Health. The government has certain rights in the invention.--

Signed and Sealed this
Fifth Day of August, 2014

Michelle K. Lee
*Deputy Director of the United States Patent and Trademark Office*